(12) United States Patent
Rahman

(10) Patent No.: US 12,400,554 B1
(45) Date of Patent: Aug. 26, 2025

(54) PATHWAY ILLUMINATION AND GUIDANCE FOR INDIVIDUALS WITH COGNITIVE IMPAIRMENT

(71) Applicant: Safi A. Rahman, Ellicott City, MD (US)

(72) Inventor: Safi A. Rahman, Ellicott City, MD (US)

( * ) Notice: Subject to any disclaimer, the term of this patent is extended or adjusted under 35 U.S.C. 154(b) by 0 days.

(21) Appl. No.: 19/060,687

(22) Filed: Feb. 22, 2025

(51) Int. Cl.
| | |
|---|---|
| *G09B 5/06* | (2006.01) |
| *G06F 3/16* | (2006.01) |
| *G06V 40/20* | (2022.01) |
| *G08B 7/06* | (2006.01) |
| *G08B 21/04* | (2006.01) |
| *G16H 40/20* | (2018.01) |
| *G10L 25/63* | (2013.01) |

(52) U.S. Cl.
CPC ............. *G09B 5/065* (2013.01); *G08B 7/066* (2013.01); *G08B 21/0423* (2013.01); *G16H 40/20* (2018.01); *G06F 3/165* (2013.01); *G06V 40/20* (2022.01); *G10L 25/63* (2013.01)

(58) Field of Classification Search
CPC . G08B 7/066; G08B 1/08; G08B 5/36; G08B 5/38; G08B 21/0423; G06V 40/20; G06F 3/165; G16H 40/20; G09B 5/065; G10L 25/63
See application file for complete search history.

(56) References Cited

U.S. PATENT DOCUMENTS

| | | | |
|---|---|---|---|
| 2023/0368881 A1* | 11/2023 | Jungnickel | ............. A46B 17/00 |
| 2024/0321068 A1* | 9/2024 | Gregorio | ............. G01C 21/206 |

* cited by examiner

*Primary Examiner* — Peter S Vasat
*Assistant Examiner* — Jaymin Jongwoo Baek

(57) ABSTRACT

Utilizing illuminated pathways to guide a user with cognitive impairment includes storing a predefined sequence of daily activities for the user; detecting a current location of the user in an indoor environment in real-time using at least one environmental sensor; activating selected light-emitting elements to create a first illuminated pathway between the current location and a first target location based on the predefined sequence of daily activities corresponding to the user; presenting at least one of task-specific audio and visual instructional content on a display device at the first target location for a current activity in the sequence; monitoring completion of the current activity through the at least one environmental sensor; deactivating the first illuminated pathway upon detecting arrival at the first target location; and advancing to a next activity in the sequence upon verifying completion of the current activity by illuminating a second pathway to a second target location.

20 Claims, 21 Drawing Sheets

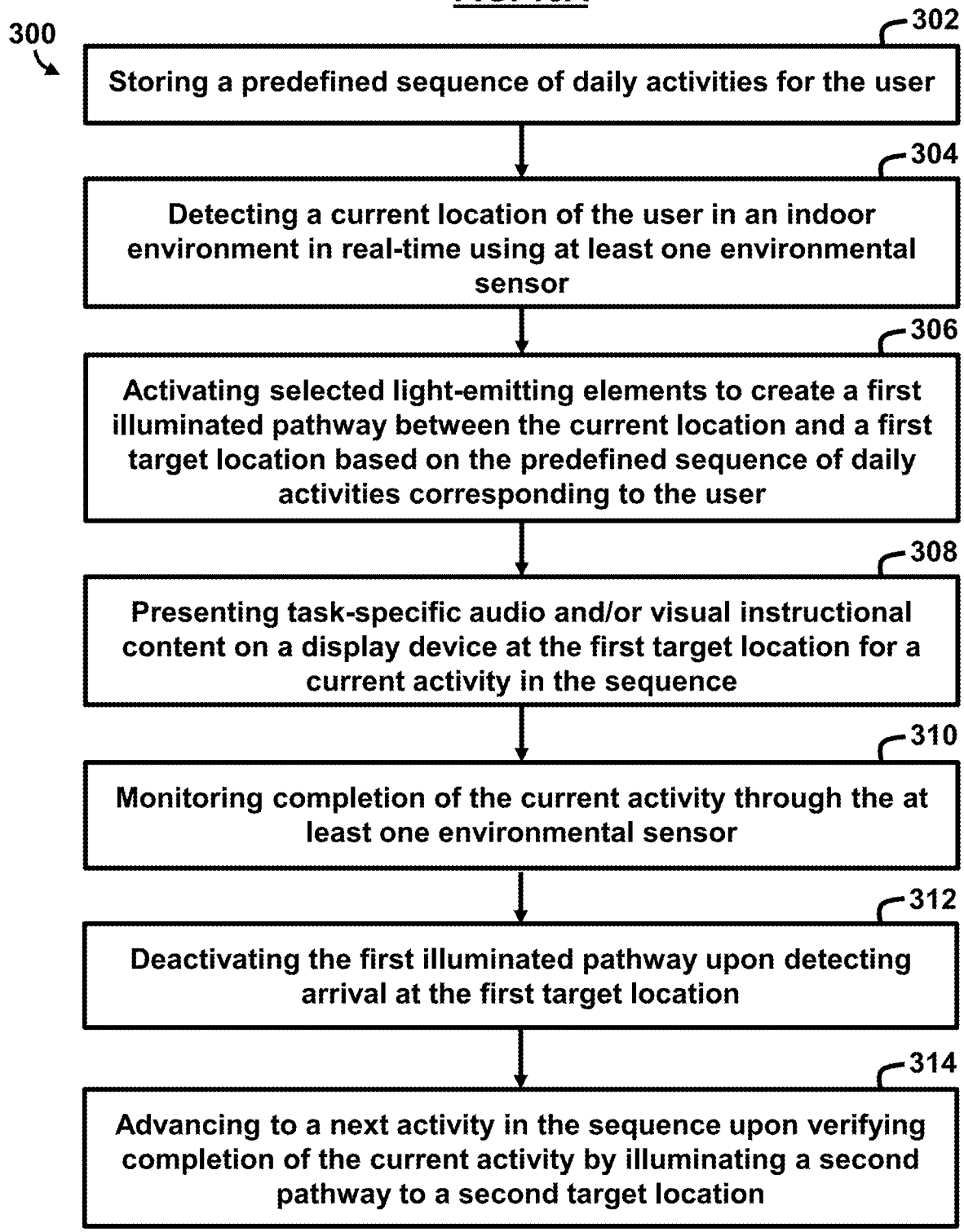

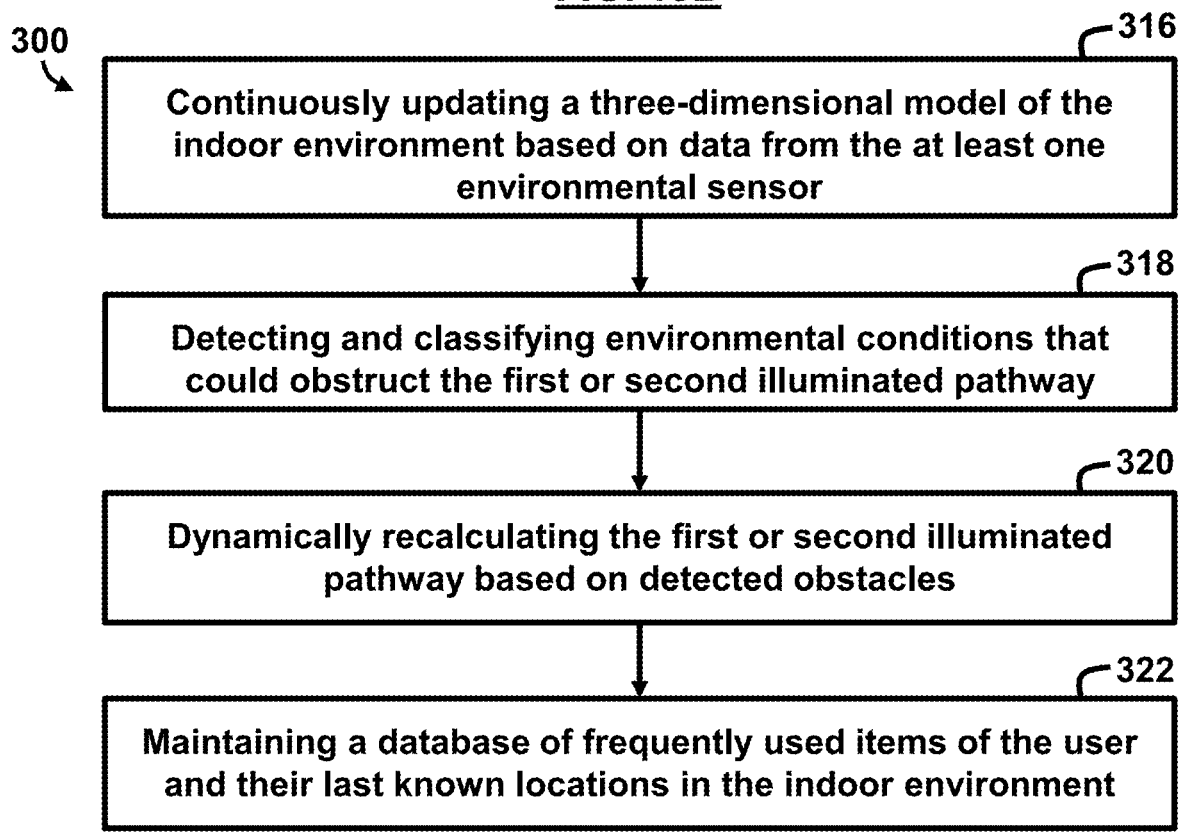

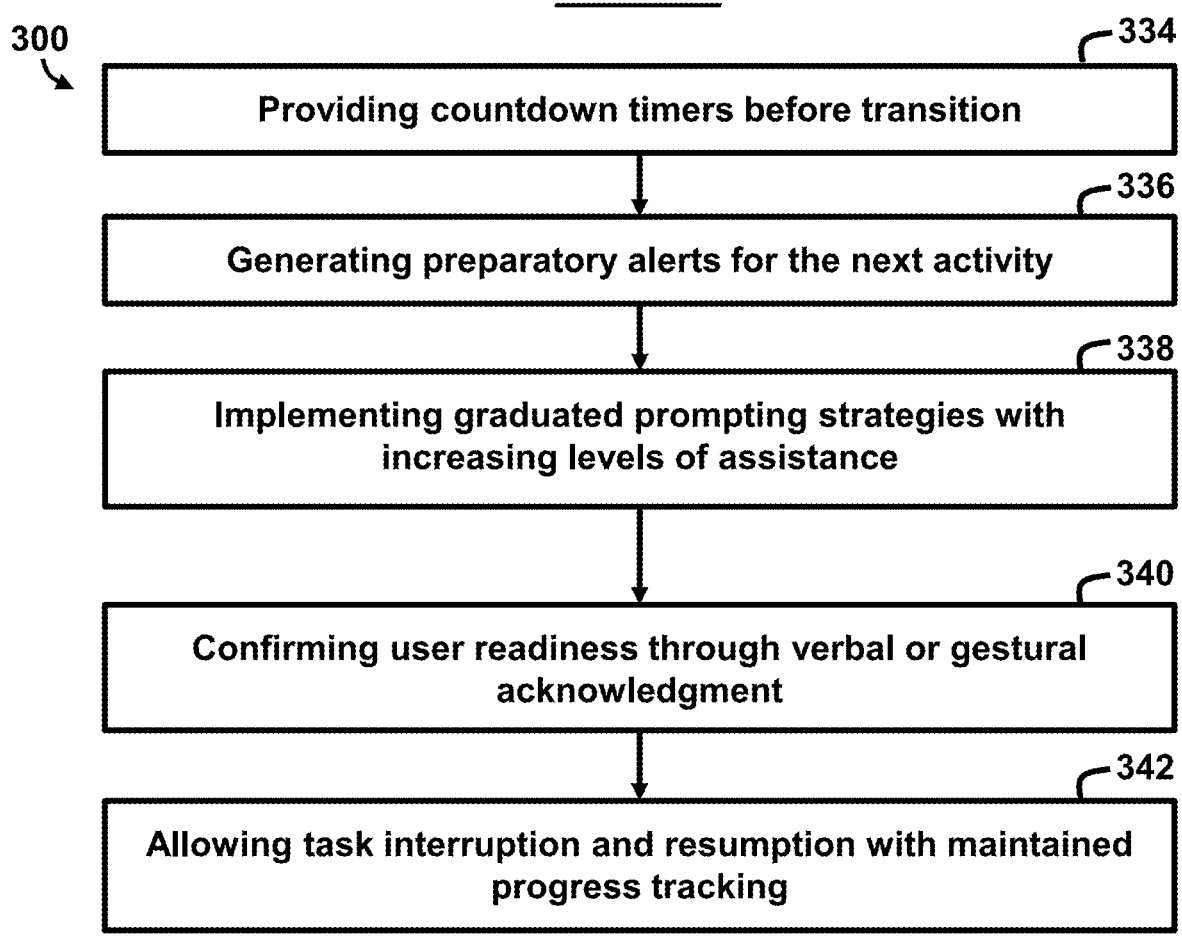

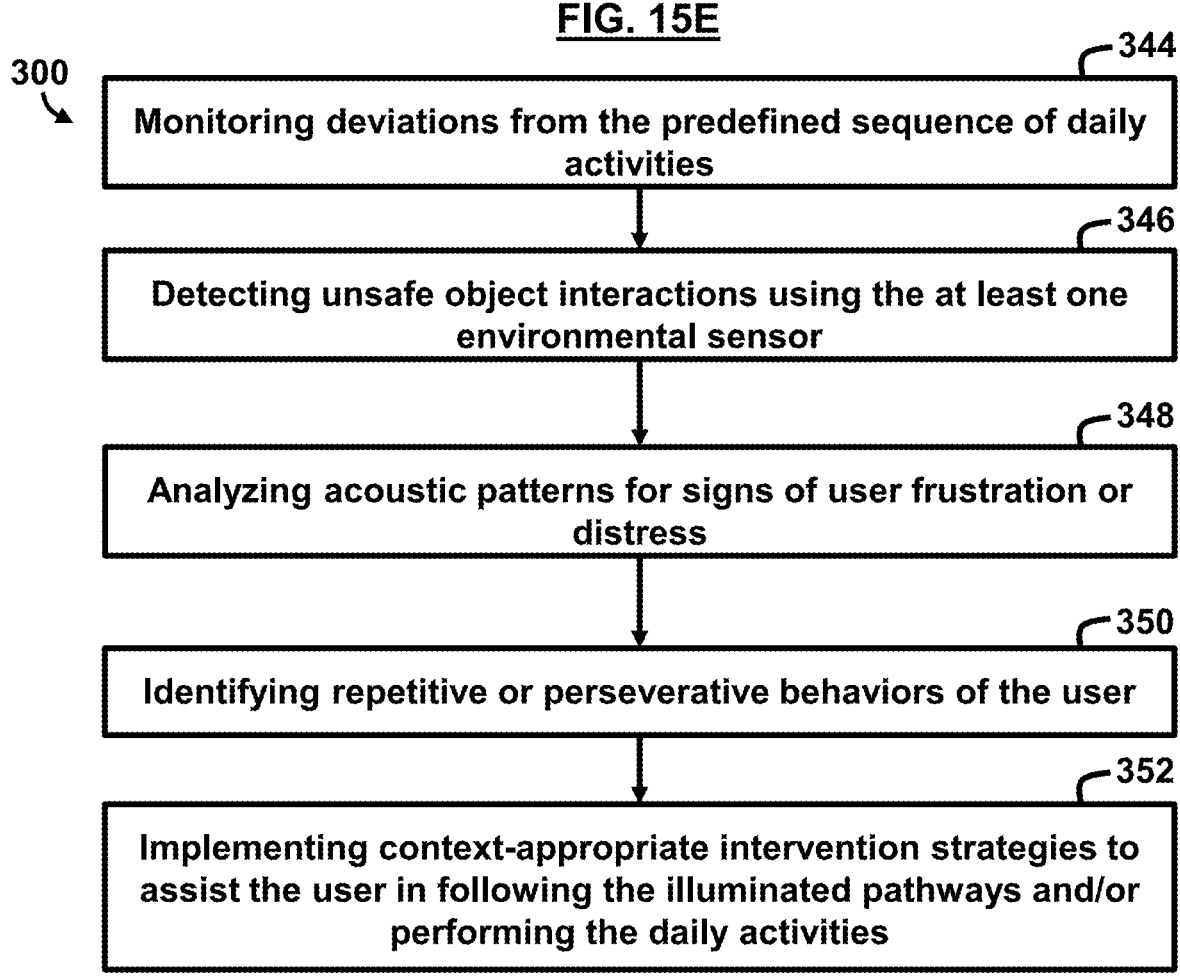

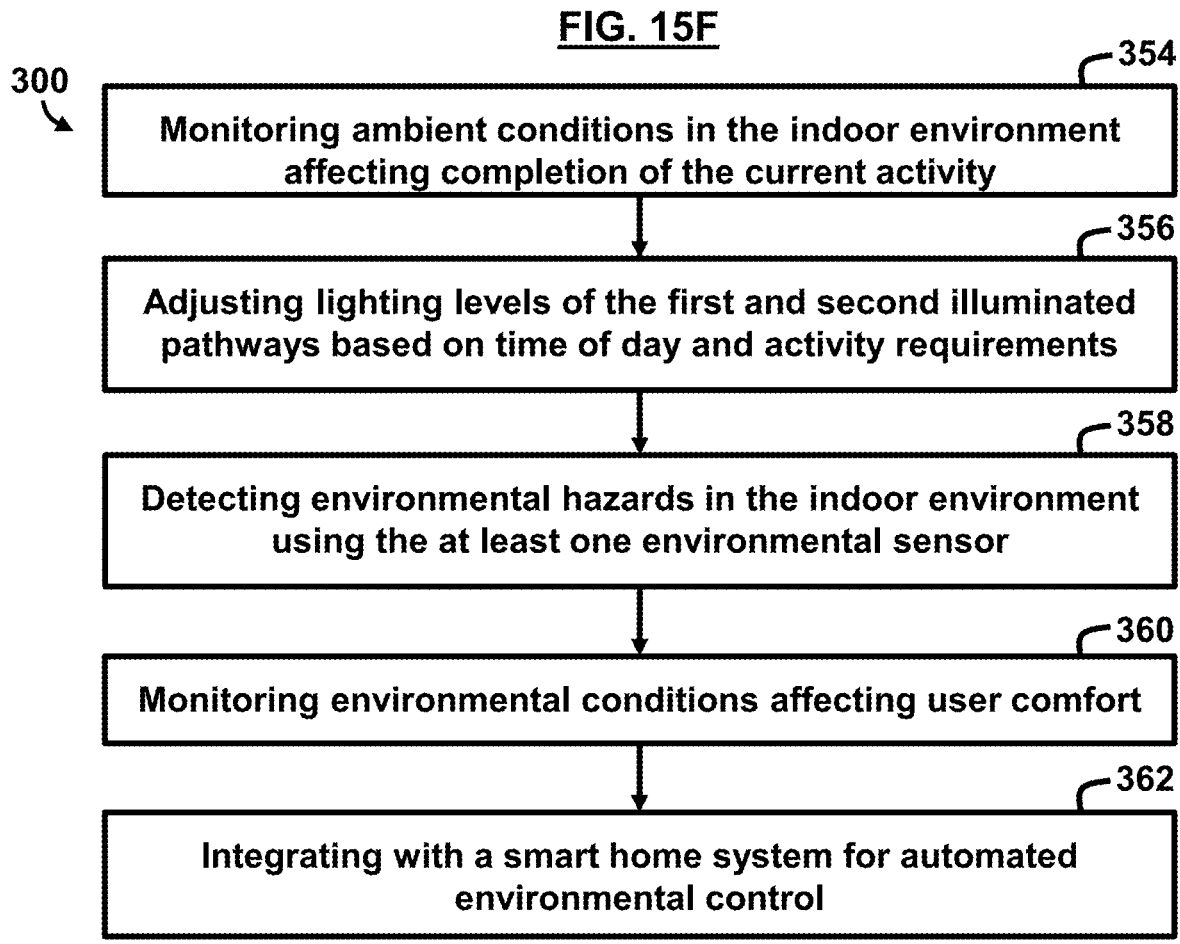

PATHWAY ILLUMINATION AND GUIDANCE FOR INDIVIDUALS WITH COGNITIVE IMPAIRMENT

BACKGROUND

Technical Field

The embodiments herein generally relate to guidance systems, and more particularly to pathway illumination and activity guidance systems for assisting individuals with cognitive impairments in navigating various environments and performing daily activities.

Description of the Related Art

This background description includes information that may be useful in understanding the present invention. It is not an admission that any of the information provided herein is prior art or relevant to the presently claimed invention or that any publication specifically or implicitly referenced is prior art.

Individuals with cognitive impairments, including those with dementia, Alzheimer's disease, autism spectrum disorders, traumatic brain injuries, intellectual disabilities, and age-related cognitive decline, face significant challenges in independently navigating their living environments and completing activities of daily living. These challenges manifest in several ways that impact quality of life and independence.

For example, spatial disorientation is a common symptom for many individuals with cognitive impairments. They frequently experience difficulty with wayfinding, even within familiar environments such as their homes. This disorientation can lead to wandering, confusion, and anxiety, especially during transitions between different locations or activities. Also, task sequencing presents substantial challenges. Many individuals struggle to remember the correct order of steps required to complete routine activities such as personal hygiene, meal preparation, or medication management. This difficulty with executive functioning often results in task abandonment, incomplete activities, or unsafe attempts at completion. Furthermore, context recognition problems can prevent individuals from associating specific locations with their corresponding activities. For example, a person may not recognize that the bathroom is where toothbrushing occurs or may forget what actions should be performed in the kitchen. Additionally, transition management between activities proves particularly problematic. Individuals with cognitive impairments often experience increased confusion and stress when moving from one activity to another, leading to perseveration on previous tasks or refusal to engage in new ones.

Moreover, environmental distractions can significantly impact focus and completion of activities. Common household stimuli may divert attention, causing individuals to lose track of their intended destination or task. Declining visual-spatial processing abilities can also make it difficult to interpret traditional signage or written instructions, limiting the effectiveness of conventional navigation and task guidance systems. In addition, temporal disorientation means many individuals lose track of time, making adherence to daily schedules challenging without frequent prompting or assistance.

Existing assistance methods predominantly rely on human caregivers providing verbal instructions and physical guidance, which limits independence and places significant burden on care providers. Alternative approaches such as static signage, written schedules, or basic reminder systems frequently prove inadequate due to the dynamic nature of cognitive impairments and the complex environmental factors affecting daily functioning.

As cognitive impairments progressively get worse, the challenges in navigation and activity completion intensify, often necessitating transition to more restrictive care environments when individuals can no longer safely navigate or perform essential activities in their homes. This progression significantly impacts quality of life and healthcare costs. Therefore, there exists a critical need for integrated solutions that address these multifaceted challenges faced by individuals with cognitive impairments in independently navigating their living environments and completing daily activities.

SUMMARY

In view of the foregoing, an embodiment herein provides a guidance system for assisting a user with a cognitive impairment, the system comprising at least one light-emitting element disposed throughout an indoor environment, wherein the at least one light-emitting element is to create illuminated pathways in the indoor environment; at least one video display device positioned at selected activity locations within the indoor environment; at least one environmental sensor disposed in the indoor environment to track user position in real time and detect environmental conditions in the indoor environment; and a processor operatively connected to the at least one light-emitting element, the at least one video display device, and the at least one environmental sensor, wherein the processor is to manage a predefined sequence of daily activities of the user; activate selected light-emitting elements to create a first illuminated pathway between a current location of the user and a first target location of the user based on the predefined sequence of daily activities; activate the at least one video display device at the first target location to present at least one of task-specific audio and visual instructional content for a current activity in the sequence; monitor completion of the current activity through the at least one environmental sensor; deactivate the first illuminated pathway upon detection of arrival of the user at the first target location; and advance to a next activity in the sequence upon verification of current activity completion by illuminating a second pathway to a second target location.

The at least one light-emitting element may comprise light-emitting diodes arranged in a strip configuration along structural components within the indoor environment. The guidance system may comprise waveguides, wherein the at least one light-emitting element comprises laser emitters that project visible light beams through the waveguides to create illuminated pathways in a plurality of angles. The guidance system may comprise reflective surfaces within the indoor environment, the reflective surfaces configured to redirect the visible light beams around corners in the indoor environment.

The processor may store multiple activity sequences for different times of day; adapt sequence timing for performing the multiple activity sequences based on user performance history; modify activity sequences based on caregiver input; and skip or modify activities based on a health status of the user. The guidance system may comprise at least one motion sensor positioned throughout the indoor environment, wherein the processor is to detect movement of the user through the at least one motion sensor; determine the current location based on the detected movement; and generate the illuminated pathways based on the current location. The task-specific instructional content may comprise pre-recorded video demonstrations of daily living activities customized for specified target locations.

The processor may access a predetermined daily routine schedule of the user; initiate activation of the illuminated pathways at predetermined times according to the daily routine schedule; and select appropriate task-specific instructional content to be presented on the at least one video display device based on time of day and specified target locations. The processor may monitor completion of the daily activities through the at least one environmental sensor; provide at least one of audio and video prompts through the at least one video display device when task completion is not detected within a predetermined time period; and send an update to a caregiver monitoring system with task completion status.

The guidance system may comprise at least one alarm operatively connected to the processor, wherein the processor is to identify irregular movement patterns or extended periods of inactivity of the user detected by at least one motion sensor based on predetermined movement patterns or the daily routine schedule; activate the illuminated pathways; send a first signal to the at least one alarm to emit at least one of an audio and video alert upon detecting the irregular movement patterns, the extended periods of inactivity of the user, or that a position of the user has deviated from the illuminated pathways; and send a second signal to designated emergency contacts. The guidance system may comprise at least one speaker positioned in the indoor environment, wherein the processor is to activate selected speakers to provide directional audio instructions along the illuminated pathways; synchronize the audio instructions with the task-specific instructional content; and adjust audio volume based on proximity to target locations.

The directional audio instructions may comprise spoken navigational instructions, musical tones that increase in frequency upon approaching the target locations, or verbal confirmations upon successful task completion, or a combination thereof. The processor may provide specific task breakdown for completing each of the daily activities; adjust an instruction detail level for performing the daily activities based on user performance; repeat instructions when user confusion is detected using input received from at least one of the at least one environmental sensor and at least one motion sensor by using a machine learning algorithm retrievable by the processor; and alert caregivers if task completion patterns indicate declining cognitive function of the user based on comparisons to learning patterns of the machine learning algorithm.

The processor may identify user-specific task completion patterns of the user; train a machine learning algorithm retrievable by the processor to establish normal task completion patterns and deviations thereof in performing the daily activities; identify early warning signs of task confusion of the user by comparing performance of completion of the daily activities compared to the established normal task completion patterns; adapt completion criteria based on user capabilities; and generate periodic cognitive assessment reports based on task performance data.

Another embodiment provides a portable guidance device for assisting a user with cognitive impairment, the device comprising a processor; a camera operatively connected to the processor; a sensor operatively connected to the processor; a projector operatively connected to the processor; a display screen operatively connected to the processor; a speaker operatively connected to the processor; and a memory storing instructions that, when executed by the processor, cause the processor to identify a current location of the user based on at least one of an image and video captured by the camera; instruct the projector to project a first illuminated pathway between the current location and a first target location based on a predefined sequence of daily activities for the user; present at least one of task-specific audio and visual instructional content through at least one of the display screen and speaker for a current activity in the sequence of daily activities; analyze activity data captured by the camera and the sensor to monitor completion of the current activity; deactivate projection of the first illuminated pathway from the projector upon detecting user arrival at the first target location; verify completion of the current activity using a machine learning algorithm that analyzes captured activity data; and instruct the projector to project a second illuminated pathway from the first target location to a second target location upon verification of completion of the current activity.

Another embodiment provides a method for utilizing illuminated pathways to guide a user with cognitive impairment, the method comprising storing a predefined sequence of daily activities for the user; detecting a current location of the user in an indoor environment in real-time using at least one environmental sensor; activating selected light-emitting elements to create a first illuminated pathway between the current location and a first target location based on the predefined sequence of daily activities corresponding to the user; presenting at least one of task-specific audio and visual instructional content on a display device at the first target location for a current activity in the sequence; monitoring completion of the current activity through the at least one environmental sensor; deactivating the first illuminated pathway upon detecting arrival at the first target location; and advancing to a next activity in the sequence upon verifying completion of the current activity by illuminating a second pathway to a second target location.

The method may comprise continuously updating a three-dimensional model of the indoor environment based on data from the at least one environmental sensor; detecting and classifying environmental conditions that could obstruct the first or second illuminated pathway; dynamically recalculating the first or second illuminated pathway based on detected obstacles; and maintaining a database of frequently used items of the user and their last known locations in the indoor environment.

The method may comprise analyzing patterns in completion of the predefined sequence of daily activities; identifying time periods of peak cognitive performance of the user based on patterns identified from a trained machine learning algorithm; automatically adjusting the predefined sequence of daily activities to align with optimal performance periods based on feedback provided by the machine learning algorithm; detecting changes in cognitive function through long-term performance tracking of user behavior corresponding to performance of the daily activities and adherence to following the illuminated pathways to travel in the indoor environment; and generating intervention alerts for healthcare providers upon detecting changes that reach a predetermined threshold.

The method may comprise managing transitions between the current activity and the next activity by providing countdown timers before transition; generating preparatory alerts for the next activity; implementing graduated prompting strategies with increasing levels of assistance; confirming user readiness through verbal or gestural acknowledgment; and allowing task interruption and resumption with maintained progress tracking. The method may comprise monitoring deviations from the predefined sequence of daily activities; detecting unsafe environmental condition interactions using the at least one environmental sensor; analyzing acoustic patterns for signs of user frustration or distress; identifying repetitive or perseverative behaviors of the user; and implementing context-appropriate intervention strategies to assist the user in following at least one of the illuminated pathways and performing the daily activities.

The method may comprise monitoring ambient conditions in the indoor environment affecting completion of the current activity; adjusting lighting levels of the first and second illuminated pathways based on time of day and activity requirements; detecting environmental hazards in the indoor environment using the at least one environmental sensor; monitoring environmental conditions affecting user comfort; and integrating with a smart home system for automated environmental control.

These and other aspects of the embodiments herein will be better appreciated and understood when considered in conjunction with the following description and the accompanying drawings. It should be understood, however, that the following descriptions, while indicating exemplary embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The embodiments herein will be better understood from the following detailed description with reference to the drawings, in which:

FIG. 15A is a flow diagram illustrating a method for utilizing illuminated pathways to guide a user with cognitive impairment, according to an embodiment herein;

FIG. 15B is a flow diagram illustrating a method for environmental mapping and dynamic path calculation, according to an embodiment herein;

FIG. 15D is a flow diagram illustrating a method for managing transitions between activities with graduated prompting strategies, according to an embodiment herein;

FIG. 15E is a flow diagram illustrating a method for monitoring deviations and implementing context-appropriate intervention strategies, according to an embodiment herein;

FIG. 15F is a flow diagram illustrating a method for monitoring environmental conditions and integrating with smart home systems, according to an embodiment herein;

Figure 1:
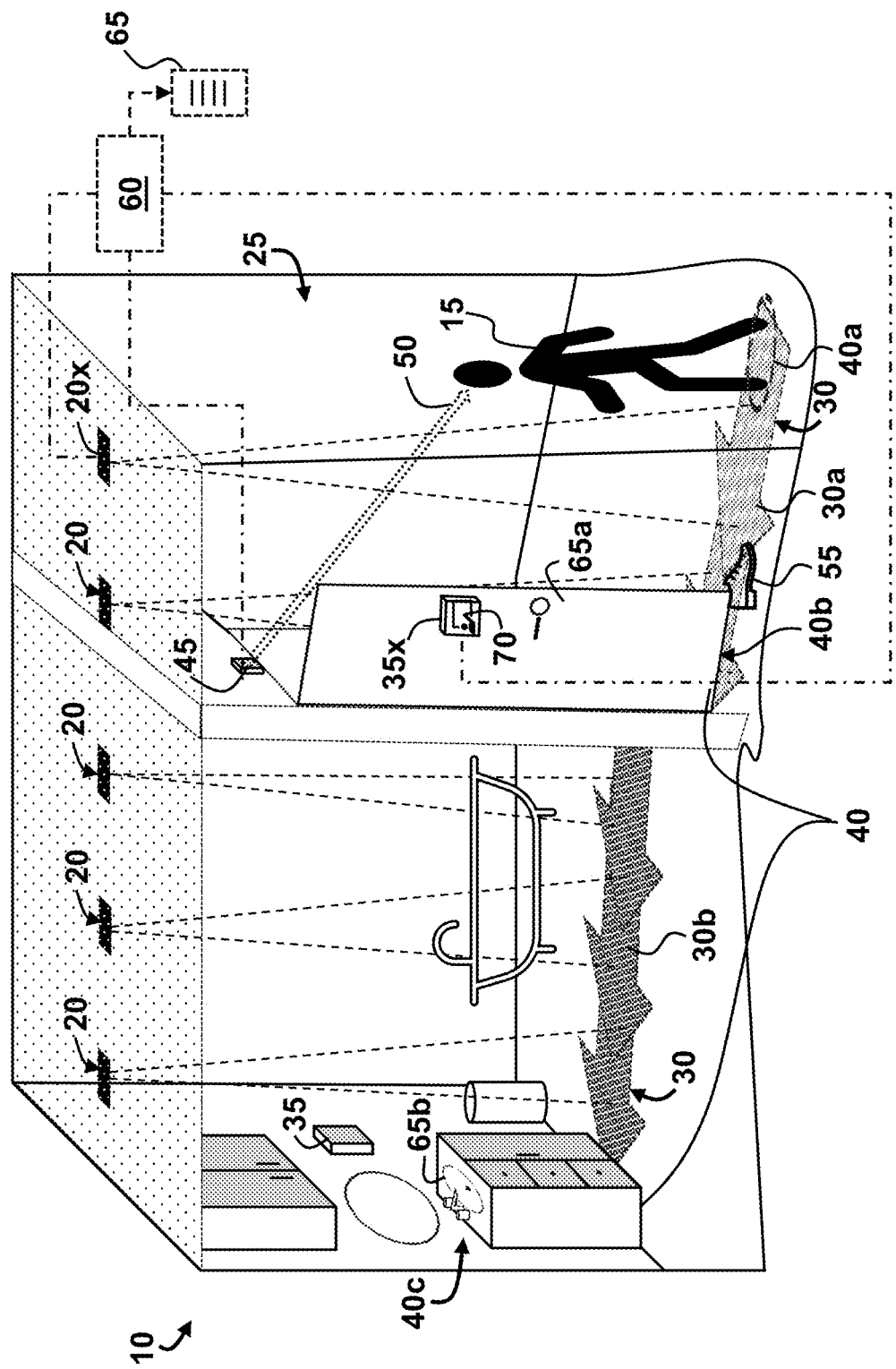
FIG. 1 is a schematic diagram illustrating a guidance system for assisting a user, according to an embodiment herein.

Throughout the drawings, identical reference numbers designate similar, but not necessarily identical, elements. The figures are not necessarily to scale, and the size of some parts may be exaggerated to more clearly illustrate the example shown. Moreover, the drawings provide examples and/or implementations consistent with the description; however, the description is not limited to the examples and/or implementations provided in the drawings.

DETAILED DESCRIPTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein. The following description of particular embodiment(s) is merely exemplary in nature and is in no way intended to limit the scope of the invention, its application, or uses, which can, of course, vary.

It will be understood that when an element or layer is referred to as being "on", "connected to", or "coupled to" another element or layer, it may be directly on, directly connected to, or directly coupled to the other element or layer, or intervening elements or layers may be present. In contrast, when an element or layer is referred to as being "directly on", "directly connected to", or "directly coupled to" another element or layer, there are no intervening elements or layers present. It will be understood that for the purposes of this disclosure, "at least one of X, Y, and Z" or "any of X, Y, and Z" may be construed as X only, Y only, Z only, or any combination of two or more items X, Y, and Z (e.g., XYZ, XY, XZ, YZ).

The description herein describes inventive examples to enable those skilled in the art to practice the embodiments herein and illustrates the best mode of practicing the embodiments herein. Upon reading the following description in light of the accompanying drawing figures, those skilled in the art will understand the concepts of the disclosure and will recognize applications of these concepts not particularly addressed herein.

The terms first, second, etc. may be used herein to describe various elements, but these elements should not be limited by these terms as such terms are only used to distinguish one element from another. For example, a first element could be termed a second element, and, similarly, a second element could be termed a first element, etc. without departing from the scope of the present disclosure. As used herein, the term "and/or" includes any and all combinations of one or more of the associated listed items.

Furthermore, the terms "final", "first", "second", "upper", "lower", "bottom", "side", "intermediate", "middle", and "top", etc. may be used herein to describe various elements, but these elements should not be limited by these terms. These terms are only used to distinguish one element from another. For example, a first element could be termed a "top" element and, similarly, a second element could be termed a "top" element depending on the relative orientations of these elements.

The terminology used herein is for the purpose of describing particular embodiments only and is not intended to be limiting of the disclosure. As used herein, the singular forms "a", "an", and "the" are intended to include the plural forms as well, unless the context clearly indicates otherwise. "Or" means "and/or." As used herein, the term "and/or" includes any and all combinations of one or more of the associated listed items. It will be further understood that the terms "comprises" and/or "comprising," or "includes" and/or "including" when used herein, specify the presence of stated features, regions, integers, steps, operations, elements, and/or components, but do not preclude the presence or addition of one or more other features, regions, integers, steps, operations, elements, components, and/or groups thereof. The term "or a combination thereof" means a combination including at least one of the foregoing elements.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

The embodiments described herein provide a guidance system, method, and device to assist cognitively impaired individuals move through an environment using illuminated pathways to serve as a guide from one location to another location. Referring now to the drawings, and more particularly to FIGS. 1A through 17, where similar reference characters denote corresponding features consistently throughout the figures, there are shown preferred embodiments. In the drawings, the size and relative sizes of components, layers, and regions, etc. may be exaggerated for clarity.

FIG. 1 illustrates a guidance system 10 for assisting a user 15 with a cognitive impairment. The system 10 comprises at least one light-emitting element 20 disposed throughout an indoor environment 25, wherein the at least one light-emitting element 20 is to create illuminated pathways 30 in the indoor environment 25; at least one video display device 35 positioned at selected activity locations 40 within the indoor environment 25; at least one environmental sensor 45 disposed in the indoor environment 25 to track user position 50 in real time and detect environmental conditions 55 in the indoor environment 25; and a processor 60 operatively connected to the at least one light-emitting element 20, the at least one video display device 35, and the at least one environmental sensor 45, wherein the processor 60 is to: manage a predefined sequence of daily activities 65 of the user 15; activate selected light-emitting elements 20$x$ to create a first illuminated pathway 30$a$ between a current location 40$a$ of the user 15 and a first target location 40$b$ of the user 15 based on the predefined sequence of daily activities 65; activate the at least one video display device 35$x$ at the first target location 40$b$ to present at least one of task-specific audio and visual instructional content 70 for a current activity 65$a$ in the sequence 65; monitor completion of the current activity 65$a$ through the at least one environmental sensor 45; deactivate the first illuminated pathway 30$a$ upon detection of arrival of the user 15 at the first target location 40$b$; and advance to a next activity 65$b$ in the sequence 65 upon verification of current activity 65$a$ completion by illuminating a second pathway 30$b$ to a second target location 40$c$.

In some examples, the processor 60 described herein and/or illustrated in the figures may be embodied as hardware-enabled modules and may be configured as a plurality of overlapping or independent electronic circuits, devices, and discrete elements packaged onto a circuit board to provide data and signal processing functionality within a computer. An example might be a RF switch, antenna tuner, comparator, inverter, or flip-flop, which could include a plurality of transistors and other supporting devices and circuit elements. The modules that are configured with electronic circuits process and/or execute computer logic instructions capable of providing digital and/or analog signals for performing various functions as described herein including controlling the operations of the system 10 and associated components. In some examples, the processor 60 may comprise a central processing unit (CPU) of a computer (not shown) operatively connected to the system 10. In other examples the processor 60 may be a discrete component independent of other processing components in the system 10. In other examples, the processor 60 may be a semiconductor-based microprocessor, microcontroller, field-programmable gate array (FPGA), hardware engine, hardware pipeline, and/or other hardware-enabled device suitable for receiving, processing, operating, and performing various functions for the system 10. The processor 60 may be provided in the system 10, coupled to the system 10, or communicatively linked to the system 10 from a remote networked location, according to various examples.

The system 10 may be embodied as an electronic device according to an example. For example, the system 10 as embodied as an electronic device may comprise any suitable type of communication device capable of transceiving data. In other examples, system 10 as embodied as an electronic device may comprise a computer, all-in-one (AIO) device, laptop, notebook computer, tablet device, mobile phone, smartphone, electronic book reader, appliance, gaming system, electronic toy, web-based server, local area network server, cloud-based server, etc., among other types of electronic devices that communicate with another device wirelessly.

Furthermore, in some examples, the system 10 may comprise various controllers, switches, processors, and circuits, which may be embodied as hardware-enabled modules and may be a plurality of overlapping or independent electronic circuits, devices, and discrete elements packaged onto a circuit board to provide data and signal processing functionality within a computer. An example might be a comparator, inverter, or flip-flop, which could include a plurality of transistors and other supporting devices and circuit elements. The modules that include electronic circuits process computer logic instructions capable of providing digital and/or analog signals for performing various functions as described herein. The various functions can further be embodied and physically saved as any of data structures, data paths, data objects, data object models, object files, and database components. For example, the data objects could include a digital packet of structured data. Example data structures may include any of an array, tuple, map, union, variant, set, graph, tree, node, and an object, which may be stored and retrieved by computer memory and may be managed by processors, compilers, and other computer hardware components. The data paths can be part of a computer CPU that performs operations and calculations as instructed by the computer logic instructions. The data paths could include digital electronic circuits, multipliers, registers, and buses capable of performing data processing operations and arithmetic operations (e.g., Add, Subtract, etc.), bitwise logical operations (AND, OR, XOR, etc.), bit shift operations (e.g., arithmetic, logical, rotate, etc.), complex operations (e.g., using single clock calculations, sequential calculations, iterative calculations, etc.). The data objects may be physical locations in computer memory and can be a variable, a data structure, or a function. Some examples of the modules include relational databases (e.g., such as Oracle® relational databases), and the data objects can be a table or column, for example. Other examples include objects, distributed objects, object-oriented programming objects, and semantic web objects. The data object models can be an application programming interface for creating HyperText Markup Language (HTML) and Extensible Markup Language (XML) electronic documents. The models can be any of a tree, graph, container, list, map, queue, set, stack, and variations thereof, according to some examples. The data object files can be created by compilers and assemblers and contain generated binary code and data for a source file. The database components can include any of tables, indexes, views, stored procedures, and triggers.

The guidance system 10 is configured for assisting a user 15 with a cognitive impairment. In the context of the embodiments herein, a user 15 may be any individual who utilizes the guidance system 10 in the manner described herein. Accordingly, the user 15 may not necessarily operate or manage the system 10, but rather is someone who utilizes or interacts with the system 10. In the context of the embodiments herein, cognitive impairments refer to any neurological deficiencies including conditions such as dementia, Alzheimer's disease, autism spectrum disorders, traumatic brain injuries, intellectual disabilities, and age-related cognitive decline, or any other condition where individuals face significant challenges in independently navigating their living environments and completing activities of daily living due to neurological deficiencies. For example, a user 15 with a cognitive impairment may be an individual with early stages of Alzheimer's, dementia, or other neurological condition who suffer some cognitive decline but who are capable of performing daily activities themselves and who may require some guidance in order to move from location to location and perform their activities. The system 10 incorporates multiple integrated components that work together to provide real-time, adaptive guidance for activities of daily living in an indoor environment 25. The guidance system 10 comprises at least one light-emitting element 20 distributed throughout the indoor environment 25, with these light-emitting elements 20 configured to create illuminated pathways 30 that provide visual guidance for navigation within the indoor environment 25.

The illuminated pathways 30 serve as intuitive visual cues that direct the user 15 along specific routes in the indoor environment 25, addressing the spatial disorientation commonly experienced by individuals with cognitive impairments. These pathways 30 utilize dynamic lighting patterns to attract attention and provide directional information without requiring the user 15 to interpret complex signage or remember multistep directions. The system's visual guidance accommodates declining visual-spatial processing abilities often present in conditions such as dementia, Alzheimer's disease, or traumatic brain injury.

At least one video display device 35 is positioned at selected activity locations 40 within the indoor environment 25. These video display devices 35 function as contextual instructional interfaces that present activity-specific guidance at precisely the locations where tasks are to be performed. This positional relationship between instruction and action location reduces the cognitive load required for context recognition and task execution.

The system 10 includes at least one environmental sensor 45 disposed throughout the indoor environment 25. These sensors 45 serve dual functions: tracking user position 50 in real time and detecting environmental conditions 55 within the indoor environment 25, which may serve as barriers or obstacles for the user 15 in moving from location to location in a safe and direct manner. The position tracking capability enables the system 10 to maintain awareness of the user's position 50, which is essential for providing relevant guidance. Environmental condition detection allows the system 10 to identify potential obstacles, hazards, or changes in ambient conditions that might affect the user's ability to navigate or complete tasks. For example, the sensors 45 may include microphones to receive audio cues from the indoor environment 25 as well as comments from the user 15. Moreover, the sensors 45 may identify ambient conditions in the indoor environment 25 such as temperature, humidity, lighting, etc.

The processor 60 provides computational management and coordination among all connected components. The various devices 20, 35, 45 may be connected through wired or wireless connections with the processor 60. The processor 60 may be located locally to the indoor environment 25 or it may be remotely located from the indoor environment 25. The processor 60 manages a predefined sequence of daily activities 65 customized for the user 15. This sequence of daily activities 65 incorporates the organization of tasks that constitute the user's daily routine, addressing challenges related to executive functioning, task sequencing, and adherence to schedules. The processor 60 maintains awareness of both completed activities and upcoming tasks, providing structure to the user's daily routine.

When guiding the user 15 between activities 65, the processor 60 activates selected light-emitting elements 20x to create a first illuminated pathway 30a. This pathway 30a connects the current location 40a of the user 15 to a first target location 40b based on the predefined sequence of daily activities 65. The illuminated pathway 30a provides continuous visual guidance, reducing the cognitive burden of wayfinding and spatial orientation for the user 15.

Upon the user's arrival at the first target location 40b, the processor 60 activates the video display device 35x positioned at this location 40b. The display device 35x presents task-specific audio and visual instructional content 70 for the current activity 65a in the sequence 65. This instructional content 70 may include step-by-step demonstrations, verbal prompts, or visual cues appropriate to the specific task, accommodating different learning styles and cognitive abilities, as well as for different languages and customs.

During task execution, the processor 60 monitors completion of the current activity 65a through inputs received from the at least one environmental sensor 45. This monitoring capability allows the system 10 to recognize when tasks have been successfully completed, when assistance may be required, or when task abandonment has occurred. The sensor 45 can detect user movements, object interactions, and environmental changes that indicate progress through the activity steps.

Once the user 15 has arrived at the first target location 40b, the processor 60 deactivates the first illuminated pathway 30a. This deactivation reduces visual distractions and helps the user 15 focus attention on the current activity rather than continuing to attend to the navigation cues. The removal of unnecessary visual stimuli helps manage the environmental distractions that often impact individuals with cognitive impairments.

After the processor 60 verifies completion of the current activity 65a through sensor inputs, it advances the guidance sequence to the next activity 65b. This advancement is physically manifested by illuminating a second pathway 30b that guides the user 15 from the first target location 40b to a second target location 40c. This sequential guidance approach supports transition management between activities, which is particularly challenging for individuals with cognitive impairments.

The illuminated pathways 30 provide continuous visual cues that reduce the cognitive load associated with navigation and wayfinding. By offering clear directional guidance, the system 10 addresses the spatial disorientation commonly experienced by individuals with cognitive impairments. The dynamic nature of these pathways 30 allows for real-time adaptation to the user's position 50 and progress.

The task-specific instructional content 70 displayed on the video display devices 35 serves as an external memory aid and procedural guide for the user 15. This content 70 compensates for deficits in prospective memory and executive functioning by providing timely, contextually relevant prompts and demonstrations. The content 70 may incorporate both visual and auditory elements to accommodate different learning preferences and sensory capabilities of the user 15.

Figure 2:
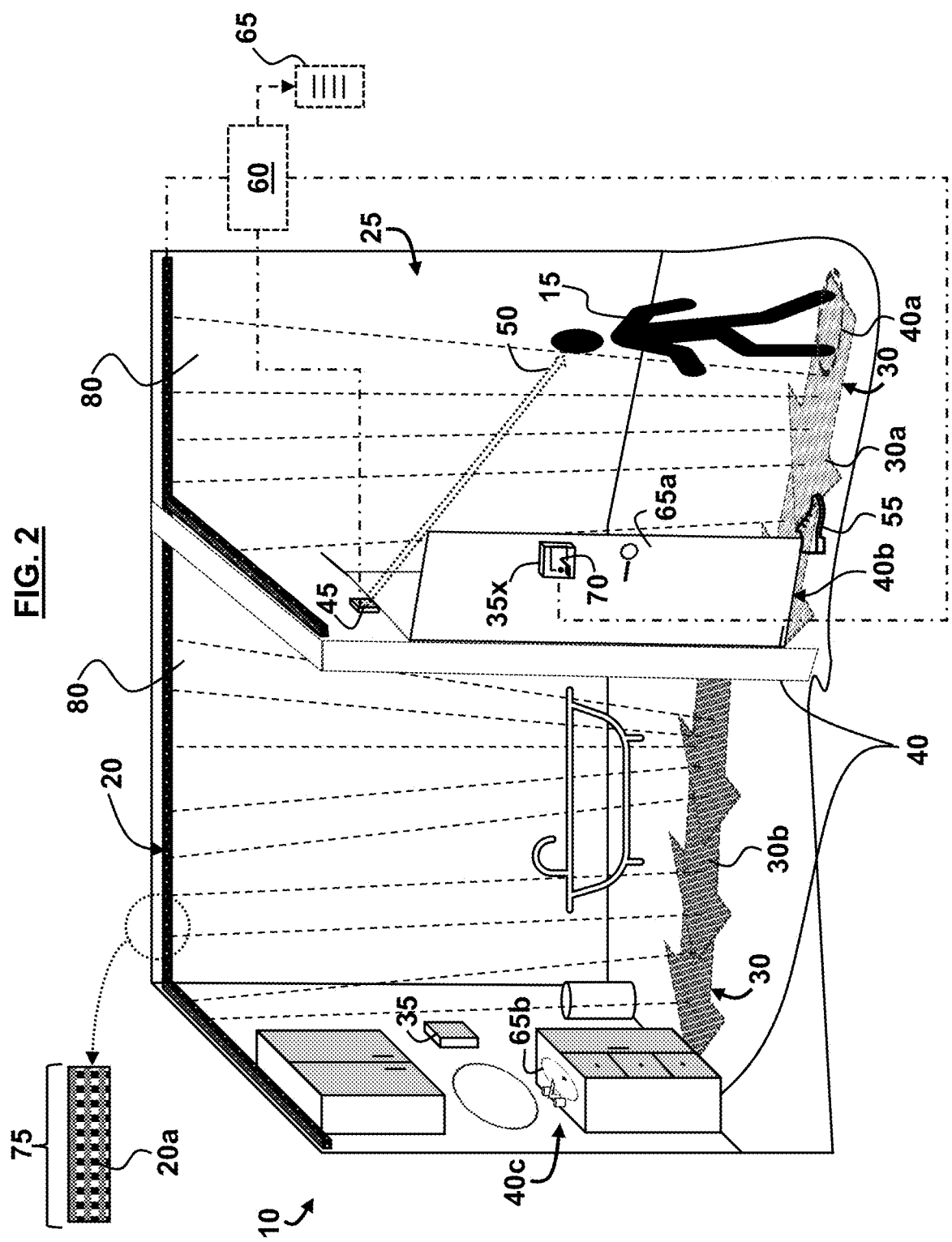
FIG. 2 is a schematic diagram illustrating a guidance system containing light-emitting diodes for generating illuminated pathways to guide a user, according to an embodiment herein.

FIG. 2, with reference to FIG. 1, illustrates that the at least one light-emitting element 20 may comprise light-emitting diodes (LEDs) 20a arranged in a strip configuration 75 along structural components 80 within the indoor environment 25. This implementation provides a practical and energy-efficient approach to creating the illuminated pathways 30 that guide users 15 through their daily activities 65.

In the context of the guidance system 10, the LEDs 20a provide directional light emission with precise optical control, enabling the creation of clearly defined pathways 30 without excessive ambient illumination that might distract or confuse the user 15. The narrow emission angle of LEDs 20a allows for concentrated light patterns that can be perceived distinctly by users 15 with visual or cognitive processing challenges. The strip configuration 75 refers to the arrangement of multiple LEDs 20a in a linear array, typically mounted on a flexible or rigid circuit board with appropriate power distribution and control circuitry. This configuration 75 enables the creation of continuous light paths that can be perceived as uninterrupted visual guides. The structural components 80 within the indoor environment 25 may include walls, floors, baseboards, door frames, ceiling edges, handrails, furniture edges, or other architectural elements that naturally define structures and pathways throughout the indoor environment 25. In an example, the LEDs 20a may generate the pathways 30 on the floor, walls, ceiling or along any other structural components 80 in the indoor environment 25.

The processor 60 can selectively activate specific segments of the LEDs 20a to create customized illuminated pathways 30 between the current location 40a of the user 15 and target locations 40b, 40c. This selective activation capability allows the system 10 to provide personalized guidance for each individual and each activity in the predefined sequence of daily activities 65. The LEDs 20a can be programmed to display different colors, intensity levels, or animation patterns (such as flowing or pulsing light) to indicate different types of activities or urgency levels. Parameters such as brightness, color temperature, contrast ratio, and animation speed can be adjusted to accommodate visual impairments that often co-occur with cognitive conditions. This adaptability ensures optimal visibility while avoiding potentially disturbing or confusing lighting effects that might exacerbate cognitive symptoms.

Figure 3:
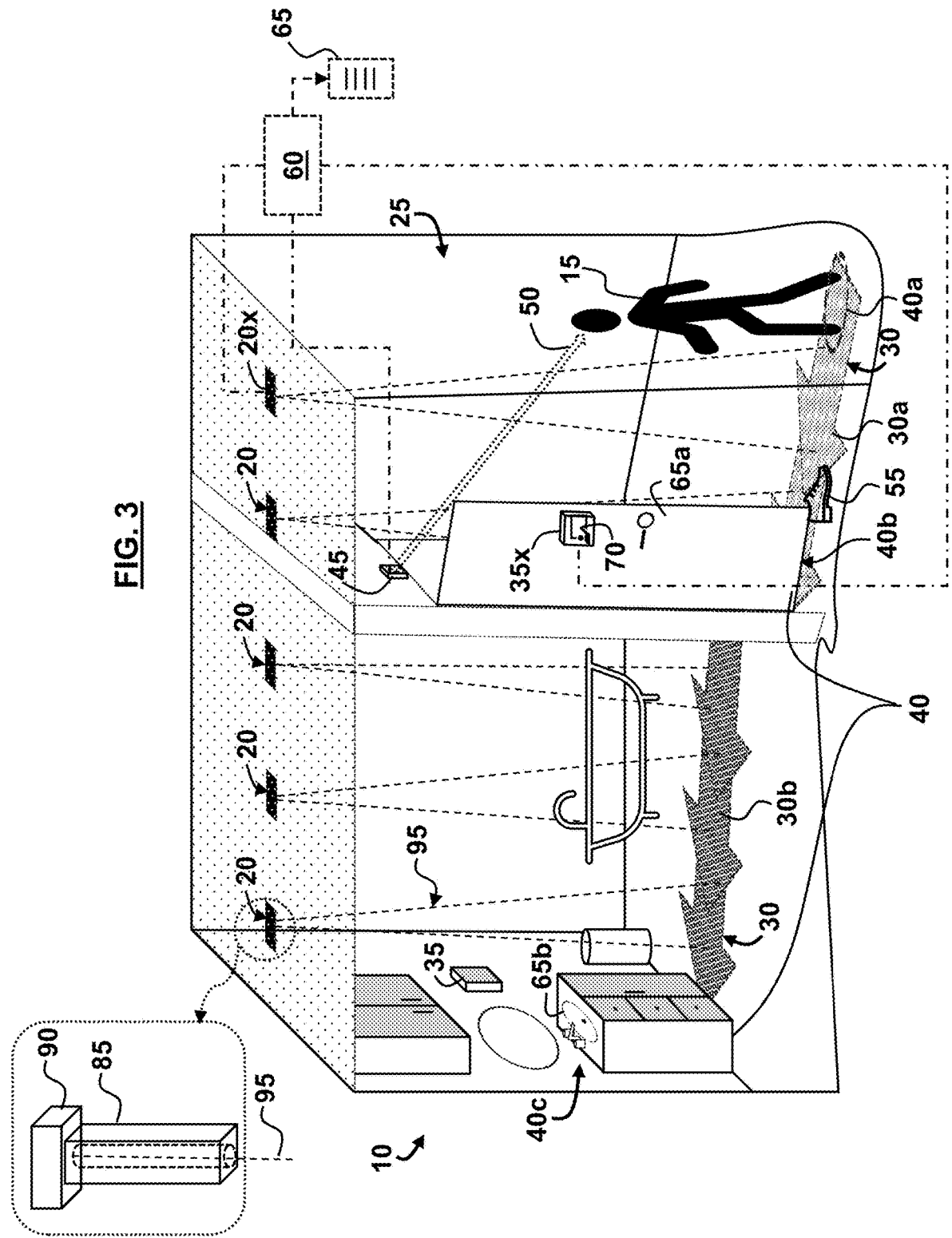
FIG. 3 is a schematic diagram illustrating a guidance system containing laser emitters for generating illuminated pathways to guide a user, according to an embodiment herein.

FIG. 3, with reference to FIGS. 1 and 2, illustrates that the guidance system 10 may comprise waveguides 85. The at least one light-emitting element 20 may comprise laser emitters 90 that project visible light beams 95 through the waveguides 85 to create illuminated pathways 30 in a plurality of angles. In the guidance system 10, the waveguides 85 may be implemented as transparent or translucent channels fabricated from materials such as acrylic, polycarbonate, or specialized optical polymers with precisely engineered optical properties. The laser emitters 90 in the guidance system 10 are configured to produce visible light within wavelength ranges optimized for perception by individuals with age-related visual changes or perceptual processing difficulties commonly associated with cognitive impairments. For example, the laser emitters 90 in the guidance system 10 may be calibrated to produce visible light within wavelength ranges of approximately 500-550 nm (green spectrum) and 570-590 nm (yellow spectrum). The visible light beams 95 produced by the laser emitters 90 are channeled through the waveguides 85. Once inside the waveguide 85, the light beam 95 propagates according to the waveguide's geometric configuration and material properties.

The waveguides 85 can create illuminated pathways 30 in a plurality of angles. The waveguides 85 themselves may be fabricated with curved or branching geometries, allowing a single light input to illuminate a complex pathway with turns, intersections, or variable widths. Also, specialized optical elements such as beam splitters, diffraction gratings, or holographic optical elements may be integrated at strategic points within the waveguide network to divide or redirect the light beams 95 into multiple paths.

The laser-waveguide configuration also enables dynamic control of pathway characteristics through modulation of the laser emitters 90. By using the processor 60 to control and vary parameters such as laser power, pulse frequency, or wavelength composition, the system 10 can alter the appearance of the illuminated pathways 30 to convey additional information. For example, increasing illumination intensity might indicate proximity to a location 40b, for example, while pulsing patterns could signal the importance or urgency of a particular activity in the predefined sequence of daily activities 65.

Figure 4:
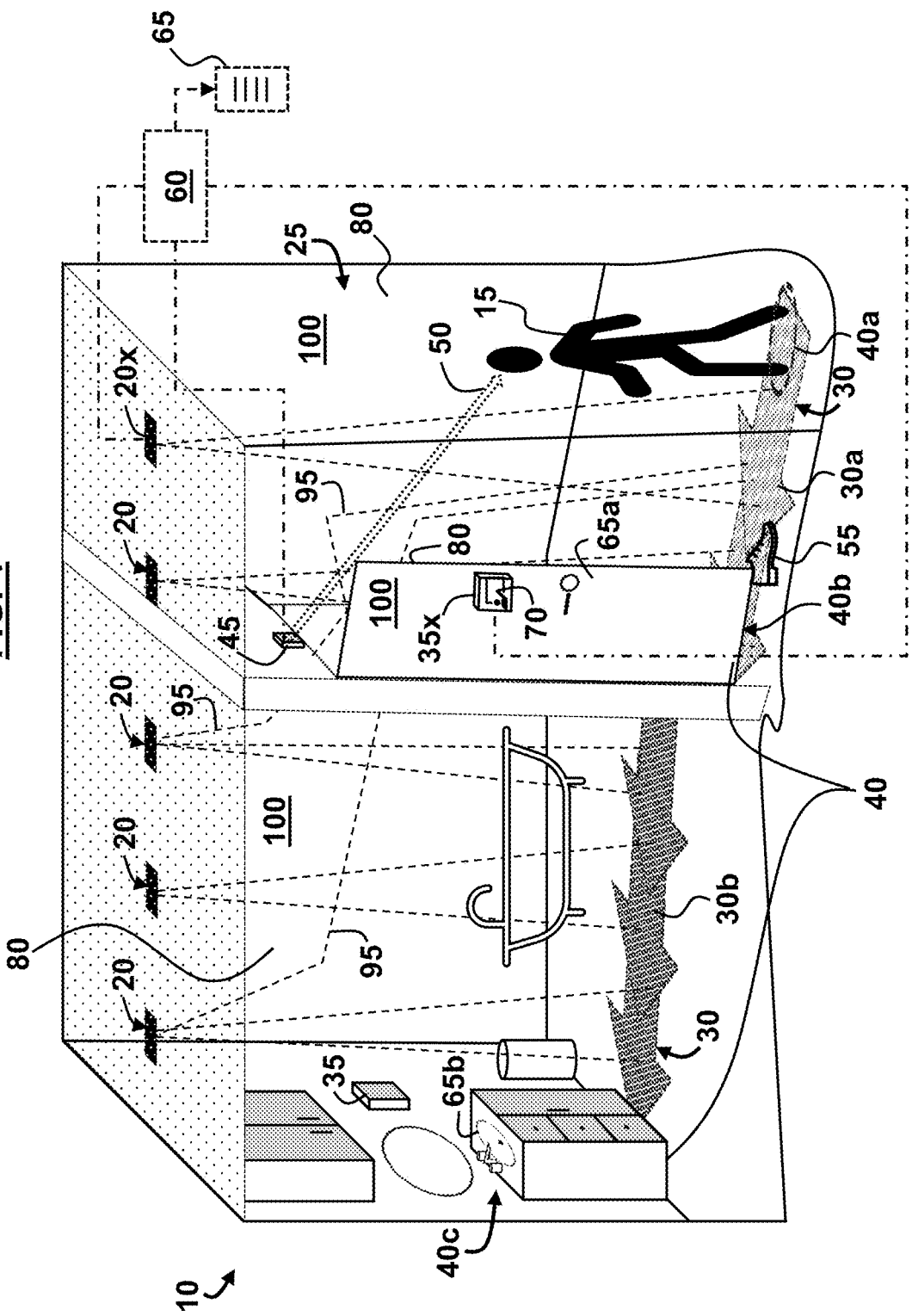
FIG. 4 is a schematic diagram illustrating a guidance system using reflective surfaces to redirect light beams, according to an embodiment herein.

FIG. 4, with reference to FIGS. 1 through 3, illustrates that the guidance system 10 may comprise reflective surfaces 100, which may be applied to structural components 80 within the indoor environment 25. The reflective surfaces 100 are configured to redirect the visible light beams 95 around corners 105 in the indoor environment 25. For example, the visible light beams 95 could also be redirected around environmental conditions 55 in the illuminated pathways 30. This redirection capability extends to navigating around environmental conditions 55 that may obstruct the illuminated pathways 30, providing a comprehensive solution for creating continuous visual guidance throughout complex indoor environments 25.

The reflective surfaces 100 represent an application of optical reflection principles to address the geometric constraints of residential environments. These surfaces 100 may be fabricated from materials with high reflectivity coefficients in the visible spectrum, such as polished aluminum (with reflectivity up to 91%), enhanced silver coatings (with reflectivity up to 98%), or dielectric mirror structures (with wavelength-specific reflectivity exceeding 99.5%).

The angle of each reflective surface 100 is determined by the relative positions of the incoming light source and the desired outgoing light path, following the principle that the angle of incidence equals the angle of reflection. For example, in a 90-degree corner 105, which is common in residential architecture, the reflective surface 100 is typically positioned at a 45-degree angle to both intersecting walls, creating a redirection of exactly 90 degrees. The material composition and surface treatment of the reflective surfaces 100 are specifically engineered for the optical properties of the visible light beams 95 produced by the laser emitters 90.

An aspect of the reflective surfaces 100 is their ability to redirect visible light beams 95 around environmental conditions 55 that may obstruct direct pathways. Environmental conditions 55 in this context may include temporary obstacles (such as furniture that has been moved), personal household items, permanent features (such as support columns or stairways), or dynamic elements (such as open doors or active appliances). The reflective surfaces 100 can be positioned on the structural components 80 to create alternative light paths that circumnavigate these obstructions while maintaining the continuity of the illuminated pathway 30.

Figure 5:
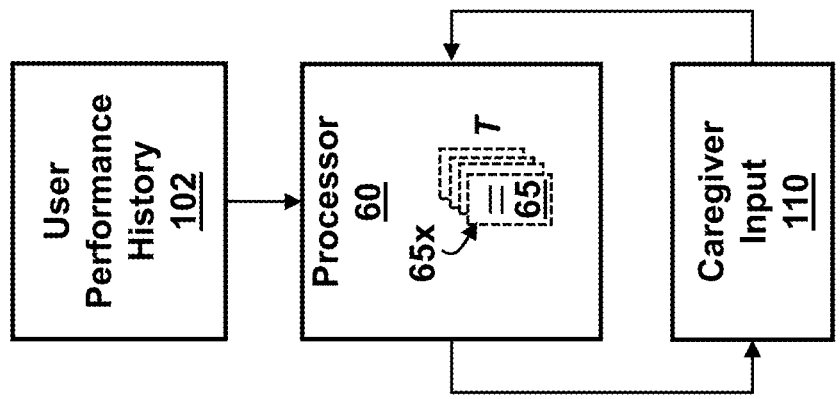
FIG. 5 is a block diagram illustrating activity sequence management based on user performance and health status, according to an embodiment herein.

FIG. 5, with reference to FIGS. 1 through 4, illustrates that the processor 60 may store multiple activity sequences 65x for different times of day; adapt sequence timing T for performing the multiple activity sequences 65x based on user performance history 102; modify activity sequences 65x based on caregiver input 110; and skip or modify activities 65 based on a health status of the user 15. The processor 60 may store multiple activity sequences 65x for different times of day, recognizing that cognitive performance, energy levels, and care needs often follow distinct patterns across different times of the day. These multiple activity sequences 65x are data structures that contain not only the sequential ordering of activities but also associated parameters such as expected duration, complexity level, prerequisite conditions, and location information for each activity. The system 10 may maintain separate morning, afternoon, and evening sequences that reflect the changing priorities and capabilities of the user 15 throughout the day. By maintaining distinct activity profiles, the system 10 accommodates the natural rhythms of daily living while providing appropriate structure for users 15 who may struggle with time perception and activity planning.

The processor 60 adapts to sequence timing T for performing the multiple activity sequences 65x based on user performance history 102. The timing parameter T represents the scheduling of activities, including their start times, durations, and the intervals between them. The user performance history 102 comprises a dataset of the user's interactions with the guidance system 10, including completion times for specific activities, patterns of assistance requirements, error rates, and deviations from expected performance. Through analysis of this historical performance data, the processor 60 can identify patterns in the user's cognitive functioning and adjust activity scheduling accordingly.

The processor 60 may modify activity sequences 65x based on caregiver input 110. In the context of the embodiments herein, caregiver input 110 represents a structured communication channel through which healthcare professionals, family members, or other care providers can influence the guidance provided by the system 10. The caregiver input 110 might include qualitative assessments of the user's cognitive state, information about scheduled appointments or special events, preferences regarding activity prioritization, or specific instructions for activity modifications.

The processor 60 is configured to skip or modify activities 65 based on the health status of the user 15. The health status represents a multidimensional assessment of the user's 15 current physical and cognitive condition, derived from various inputs including environmental sensors 45, wearable health monitoring devices, electronic health record integrations, or direct user feedback. The health status may include parameters such as mobility level, fatigue indicators, pain assessments, medication effects, or cognitive fluctuations that might affect the user's ability to complete planned activities.

For example, detected mobility limitations might trigger the substitution of seated activities for those requiring standing, or the insertion of rest periods between physically demanding tasks. Indications of increased cognitive confusion might prompt the system 10 to simplify activity instructions, increase repetition of prompts, or reschedule complex tasks to periods when the user typically demonstrates better cognitive function. These modifications may be implemented dynamically and in real-time, allowing the system 10 to respond to changes in health status throughout the day rather than requiring predefined alternative sequences for all possible health conditions.

Figure 6:
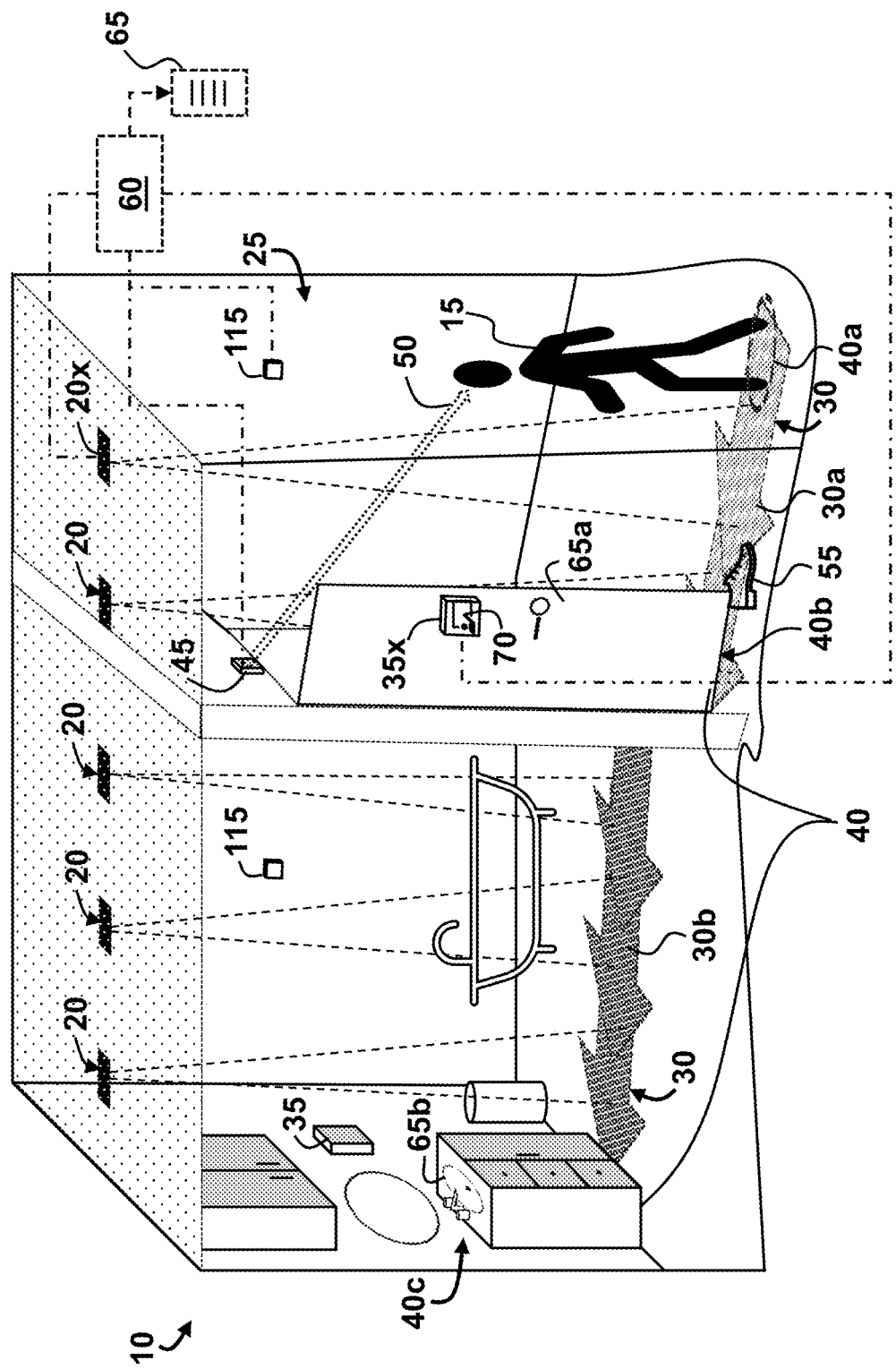
FIG. 6 is a schematic diagram illustrating a guidance system containing a motion sensor to detect movement of a user, according to an embodiment herein.

FIG. 6, with reference to FIGS. 1 through 5, illustrates that the guidance system 10 may comprise at least one motion sensor 115 positioned throughout the indoor environment 25, wherein the processor 60 is to detect movement of the user 15 through the at least one motion sensor 115; determine the current location 40a based on the detected movement; and generate the illuminated pathways 30 based on the current location 40a. Motion sensors 115, in the context of the guidance system 10, refer to electronic devices capable of detecting physical movement within their detection field and converting this movement into electrical signals for processing. The positioning of motion sensors 115 throughout the indoor environment 25 creates a comprehensive detection field that minimizes blind spots while optimizing spatial resolution. Sensors 115 may be selectively mounted on structural components 80 to maximize detection efficiency for typical human movement patterns.

The processor 60 implements algorithms to detect movement of the user 15 through the at least one motion sensor 115. The detection process begins with signal acquisition, where the processor 60 continuously samples the electrical outputs from all connected motion sensors 115 at a frequency sufficient to capture natural human movement (typically 5-20 Hz). These raw signals undergo primary processing, including noise filtering to remove environmental interference, signal normalization to compensate for variations in sensor sensitivity, and baseline correction to account for ambient conditions. The processed signals are then analyzed for patterns indicative of human movement as opposed to other environmental changes such as shifting sunlight, air currents, or pet activity.

Following movement detection, the processor 60 performs spatial analysis to determine the current location 40a of the user 15 based on the detected movement. This localization process requires triangulation across multiple sensor inputs and mapping of detection patterns onto a spatial model of the indoor environment 25. The localization algorithm maintains a continuously updated position estimate, tracking the user 15 as they move through the indoor environment 25. This tracking function incorporates motion prediction based on physical models of human movement, allowing the system 10 to maintain position awareness during brief sensor occlusions or in areas with reduced sensor coverage.

Once the current location 40a has been determined, the processor 60 generates the illuminated pathways 30 based on this location information. The pathway generation process identifies the appropriate target location (e.g., location 40b) for guidance based on the current position 50 of the user 15 within the predefined sequence of daily activities 65. Then, the optimal route between the current location 40a and the identified target location 40b is identified, considering factors such as distance, accessibility, familiarity, and potential obstructions due to environmental conditions 55. Next, the processor 60 generates specific illumination commands for the light-emitting elements 20 that creates the illuminated pathway 30.

The illuminated pathway generation may employ dynamic adaptation based on the user's position 50 and movement. As the user 15 progresses along the illuminated pathway 30, the system 10 may implement sequencing techniques where pathway segments illuminate progressively ahead of the user's position, creating an effect that encourages forward movement. The pathway brightness or color characteristics may adjust based on proximity to decision points or destinations, providing subtle cues about remaining distance or upcoming directional changes. For users 15 who demonstrate hesitation or confusion, the system 10 may emphasize the pathway illumination by providing flashing lights, etc. or activate other types of cues to reinforce the guidance.

A unique aspect of the motion-based guidance approach is its ability to provide spontaneous assistance without requiring deliberate user activation. This is helpful for users 15 with cognitive impairments, who may not consistently remember how to request assistance or may not recognize when assistance is needed. By continuously monitoring user position 50 and initiating guidance when appropriate based on the current location 40a and activity context, the system 10 provides support precisely when needed without imposing additional cognitive demands on the user 15.

Figure 7:
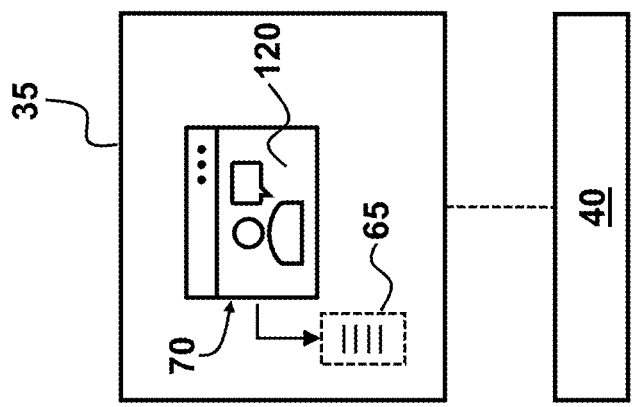
FIG. 7 is a block diagram illustrating video demonstrations displayed on a video display device, according to an embodiment herein.

FIG. 7, with reference to FIGS. 1 through 6, illustrates that the task-specific instructional content 70 may comprise pre-recorded video demonstrations 120 of daily living activities 65 customized for specified target locations 40. The pre-recorded video demonstrations 120 are multimedia instructional units that visually depict the proper execution of daily living activities 65 such as personal hygiene, meal preparation, medication management, household maintenance, or leisure activities.

An aspect of these video demonstrations 120 is their customization for specified target locations 40 within the user's actual living environment 25. Unlike generic instructional videos that depict standardized environments, the pre-recorded demonstrations for the guidance system 10 are captured within the user's own indoor environment 25, using the actual structural components 80 and fixtures, appliances, furniture, and other objects that the user 15 will interact with during task performance. The content 70 of the pre-recorded video demonstrations 120 provides individual steps presented with clear visual delineation between sequential actions. The content 70 may be presented at a slightly reduced speed (typically 80-90% of normal execution speed) to allow for adequate processing time, particularly for complex motor sequences. Pauses between sequential steps are dynamically adjusted based on step complexity, with longer pauses following actions that involve multiple components or require significant cognitive processing. This adaptive pacing accommodates the reduced processing speed and increased comprehension time often required by individuals with cognitive impairments.

Audio components of the pre-recorded video demonstrations 120 are developed for cognitive accessibility. Narration employs simplified linguistic structures with controlled vocabulary appropriate for the user's comprehension level and language abilities. Verbal instructions are delivered significantly slower than conventional instructional narration to allow for cognitive processing by the user 15. The audio frequency range is concentrated in the 500-3000 Hz band, which remains most accessible even for individuals with age-related hearing changes, with reduced content in higher frequencies that might be less perceptible or more distorted for older adults.

An aspect of the video demonstrations 120 is their integration with the specified target locations 40 where activities will be performed. The video display devices 35 positioned at these locations present the demonstrations in direct physical proximity to the action space, minimizing the need for the user 15 to transfer visual attention between instruction and implementation. This spatial contiguity reduces cognitive load by eliminating the mental translation typically required when instructions are presented in a location separate from the activity area.

The customization of video demonstrations 120 for specified target locations 40 extends beyond mere visual matching to include procedural adaptation for the specific equipment and environmental constraints present in each location. For example, a demonstration of sink usage would incorporate the exact faucet operation mechanism present in the user's bathroom, whether it involves knobs, levers, or motion sensors. Similarly, demonstrations of appliance operation would reflect the specific models and control configurations present in the user's environment 25.

Figure 8:
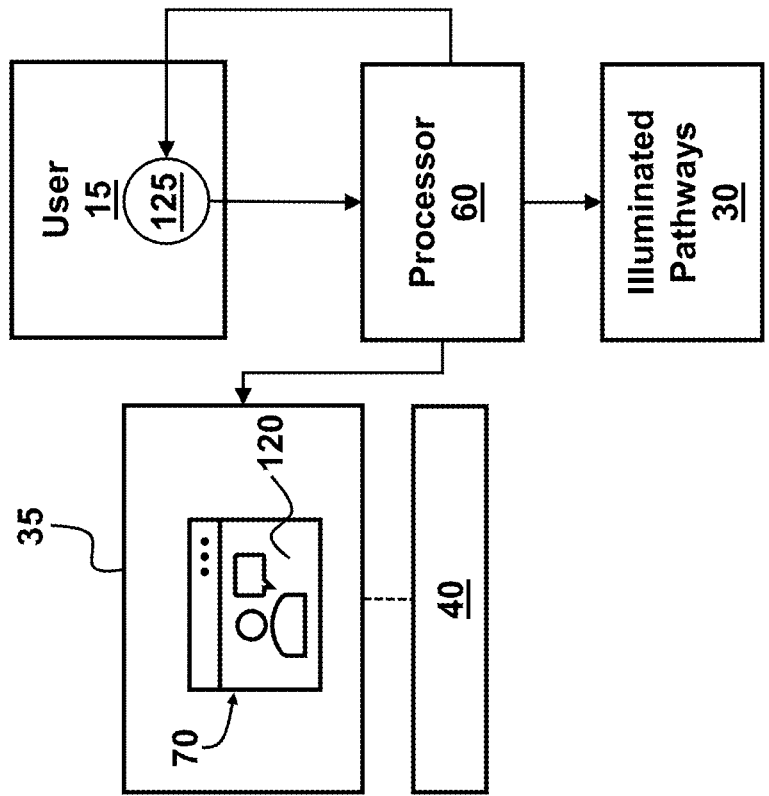
FIG. 8 is a block diagram illustrating a daily routine schedule management technique for activating illuminated pathways and selecting instructional content, according to an embodiment herein.

FIG. 8, with reference to FIGS. 1 through 7, illustrates that the processor 60 may access a predetermined daily routine schedule 125 of the user 15; initiate activation of the illuminated pathways 30 at predetermined times according to the daily routine schedule 125; and select appropriate task-specific instructional content 70 to be presented on the at least one video display device 35 based on time of day and specified target locations 40. The processor 60 may access a predetermined daily routine schedule 125 of the user 15, which serves as a framework for organizing and triggering guidance activities. The daily routine schedule 125 is a comprehensive data structure that encodes patterns of the user's regular activities 65, including their typical sequence, timing, duration, and variability parameters. This schedule 125 is not merely a simple timeline but rather a complex representation that captures both the explicit timing of critical activities (such as medication administration or meals) and the relational timing of sequential activities that may not have fixed clock times.

The daily routine schedule 125 is constructed through a combination of methods that ensure accurate representation of the user's established patterns while accommodating therapeutic goals and caregiver workflows. Initial schedule development may involve analysis of historical behavioral data collected during a baseline monitoring period, identifying recurring patterns in the user's unprompted activities. Another function of the processor 60 is the ability to initiate activation of the illuminated pathways 30 at predetermined times according to the daily routine schedule 125. This function requires the integration of precise tracking with contextual awareness of the user's current state and position 50. The activation process begins with monitoring, where the processor 60 continuously evaluates the current time against scheduled activity start times, and prepares for upcoming transitions before their scheduled initiation. As scheduled activity times approach, the system 10 enters a pre-activation phase, assessing the user's current position 50 and activity state through environmental sensors 45 and motion sensors 115 to determine the appropriate timing and manner of illuminating the pathways 30.

The schedule-based pathway activation includes multiple feedback mechanisms to address scenarios where users do not respond to initial guidance cues. If environmental sensors 45 detect that the user 15 has not begun movement toward the illuminated pathway 30 within a predefined response window, the system 10 may implement a graduated prompting strategy. This might begin with subtle intensification of the pathway illumination, progress to activation of supplementary cues such as gentle audio prompts, and ultimately escalate to more direct prompting if the lack of response continues beyond defined thresholds. Throughout this escalation process, the system 10 continues to monitor for user movement, immediately responding to any detected initiation of activity by providing appropriate guidance for the user's current position 50.

The processor 60 is configured to select appropriate task-specific instructional content 70 to be presented on the at least one video display device 35 based on time of day and specified target locations 40. This content selection function represents an integration of context, spatial awareness, and instructions. The processor 60 evaluates multiple parameters to identify the most appropriate instructional content for each specific guidance instance, ensuring that the provided instruction matches both the scheduled activity and the user's current cognitive and functional state.

The time-of-day parameter in content selection enables the system 10 to accommodate variations in cognitive functioning, energy levels, and assistance requirements that are common in individuals with cognitive impairments. For example, morning medication management instruction might include detailed dosage information and medication recognition cues, while evening medication instruction might incorporate additional reminders and verification steps to accommodate typical evening increases in confusion. The processor 60 implements content preparation mechanisms to ensure timely delivery of selected instructional content 70 when the user 15 arrives at the specified target locations 40. As scheduled activity times approach, the system 10 pre-loads relevant instructional content 70 for playback on the appropriate video display devices 35, minimizing potential latency between pathway arrival and instruction presentation, which would ordinarily enhance user confusion and irritation.

A feature of the schedule-based content selection is its ability to provide contextually appropriate variations of instructions for the same activity based on context. For example, morning hygiene routines might receive different instructional emphasis than evening hygiene, with morning instruction focusing on thoroughness and proper technique while evening instruction might emphasize completion of critical elements while accommodating increased fatigue. Similarly, meal preparation instruction might vary based on meal type and complexity appropriate to different times of day.

Figure 9:
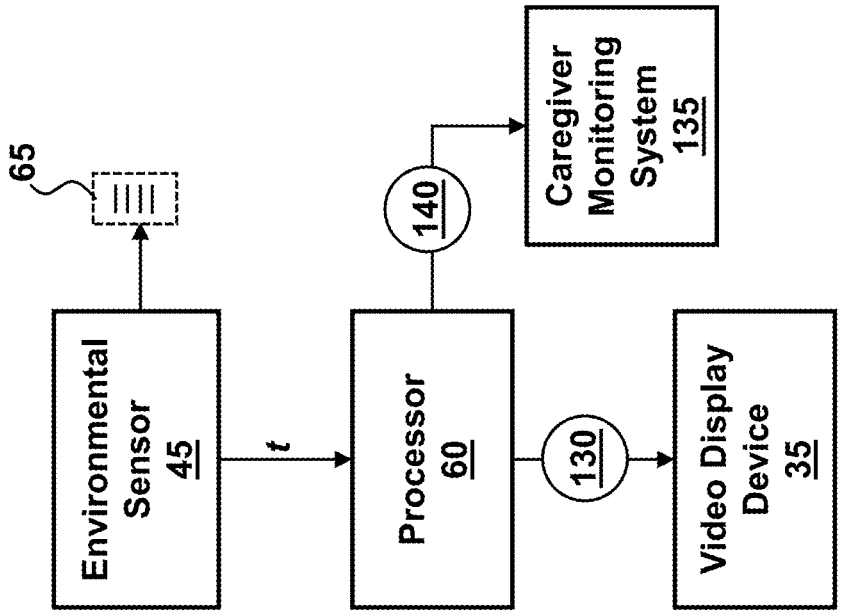
FIG. 9 is a block diagram illustrating a technique for monitoring completion of daily activities, according to an embodiment herein.

FIG. 9, with reference to FIGS. 1 through 8, illustrates that the processor 60 may monitor completion of the daily activities 65 through the at least one environmental sensor 45; provide at least one of audio and video prompts 130 through the at least one video display device 35 when task completion is not detected within a predetermined time period t; and send an update to a caregiver monitoring system 135 with task completion status 140. The processor 60 integrates data from multiple environmental sensors 45, which may include motion detectors, pressure sensors, contact switches, flow meters, temperature sensors, power consumption monitors, or specialized sensors for specific appliances and fixtures.

The processor 60 may process raw sensor data through signal conditioning algorithms that filter noise, normalize variations in sensor response, and extract relevant features from data streams. These processed signals are analyzed to identify characteristic patterns associated with particular task components. Statistical pattern recognition or machine learning trained on extensive datasets of typical task performance patterns may be utilized.

When the processor 60 detects that task completion is not occurring within the predetermined time period t, the processor 60 activates its prompting functionality to provide at least one of audio and video prompts 130 through the at least one video display device 35. The predetermined time period t is not a single fixed value but rather a context-dependent parameter that varies based on multiple factors. These factors may include the specific activity type and its criticality, the user's historical performance patterns for similar tasks, the time of day, and any detected environmental factors that might legitimately affect task timing.

The prompts 130 delivered through the video display device 35 occur in a deliberate manner. Rather than immediately providing comprehensive instruction, the system 10 may begin with minimal cues and progressively increase cues based on continued monitoring of user response. Initial prompts 130 might be subtle audiovisual cues that redirect attention to the task without explicit instruction. If monitoring indicates continued lack of progress, the system 10 may escalate to more specific prompts highlighting the next required action. If environmental sensors 45 detect that the user's attention has diverted to a non-task element (such as an environmental distraction, etc.), the system 10 may repeat prompts to gently redirect focus to the task at hand.

The processor 60 is configured to send an update to a caregiver monitoring system 135 with task completion status 140. This communication functionality creates an information bridge between the automated guidance system 10 and healthcare professionals or family members. The caregiver monitoring system 135 represents an external system or communication device that may be accessed by authorized caregivers, family members, or healthcare providers who support the user's daily functioning and well-being.

The task completion status 140 may include identification of the specific activity, its scheduled and actual start times, completion status (completed, in progress, abandoned, or rescheduled), and timestamp information. Furthermore, the status 140 may include performance metrics such as completion duration, number and type of prompts required, deviation from expected execution patterns, or specific steps that presented challenges. For incomplete activities, the status 140 includes specific information about the point of abandonment and any detected environmental or behavioral factors that may have contributed to the incomplete execution.

Figure 10:
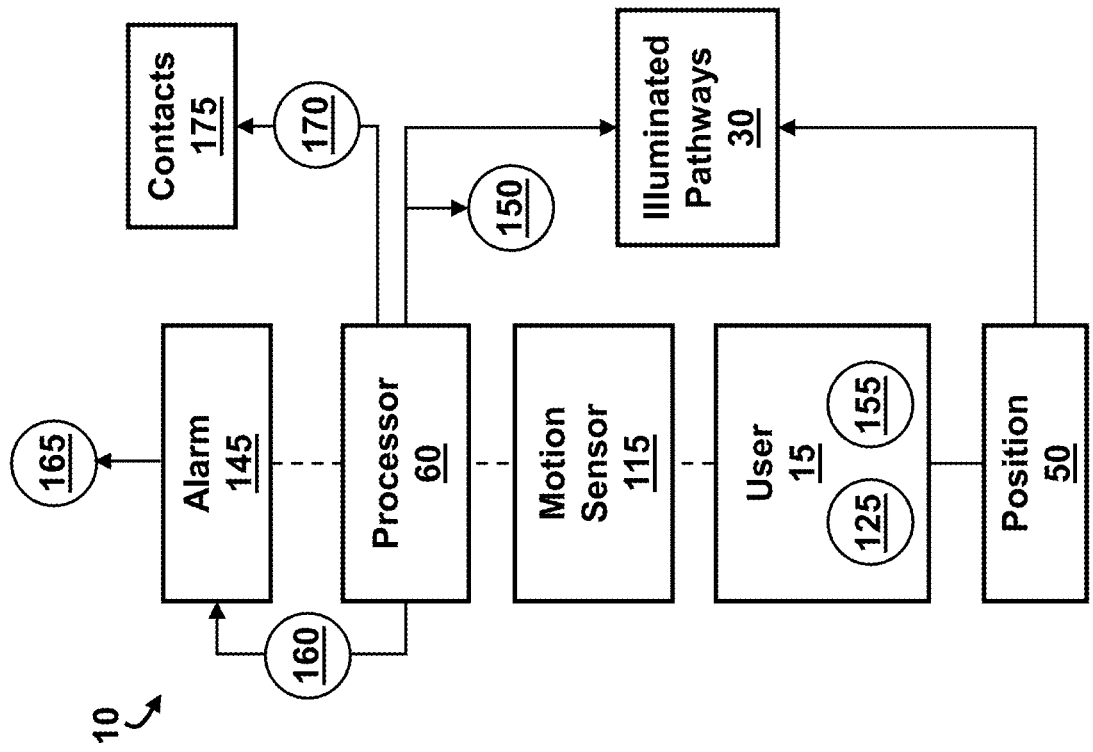
FIG. 10 is a schematic diagram illustrating a guidance system containing an alarm for emitting alerts, according to an embodiment herein.

FIG. 10, with reference to FIGS. 1 through 9, illustrates that the guidance system 10 may comprise at least one alarm 145 operatively connected to the processor 60, wherein the processor 60 is to identify irregular movement patterns 150 or extended periods of inactivity of the user 15 detected by at least one motion sensor 115 based on predetermined movement patterns 155 or the daily routine schedule 125; activate the illuminated pathways 30; send a first signal 160 to the at least one alarm 145 to emit at least one of an audio and video alert 165 upon detecting the irregular movement patterns 150, the extended periods of inactivity of the user 15, or that a position 50 of the user 15 has deviated from the illuminated pathways 30; and send a second signal 170 to designated emergency contacts 175.

The processor 60 is programmed to identify irregular movement patterns 150 or extended periods of inactivity of the user 15 detected by at least one motion sensor 115. This identification process utilizes pattern recognition algorithms that evaluate real-time movement data against reference frameworks: predetermined movement patterns 155 and the daily routine schedule 125. Predetermined movement patterns 155 comprise a baseline behavioral model specific to the individual user 15, incorporating their typical locomotion characteristics, activity rhythms, and spatial usage patterns within the indoor environment 25. These patterns are established through a multi-phase learning process during system initialization and continuously refined during operation. The system 10 employs context-aware inactivity assessment that considers the user's location, time of day, preceding activities, and established rest patterns.

The daily routine schedule 125 provides a framework of anticipated activities 65 and locations throughout the day, enabling the system 10 to distinguish between movements that are irregular but aligned with scheduled activities and those that represent genuine deviations from expected patterns. This schedule integration enables more nuanced anomaly detection that accommodates planned variations in daily activities while remaining sensitive to unexpected deviations that might indicate disorientation, wandering, or other safety concerns.

Upon detecting movement anomalies or concerning inactivity, the processor 60 initiates a multi-component response sequence. The first component of this response is to activate the illuminated pathways 30, providing visual guidance that may help reorient a user 15 experiencing spatial confusion or wandering behavior. In this context, the pathway routing may prioritize guiding the user to a designated "safe" location such as a primary living area where orientation cues are maximized, rather than continuing with scheduled activity routing.

Concurrent with pathway activation, the processor 60 sends a first signal 160 to the at least one alarm 145. This signal 160 contains specific information about the detected anomaly, including its classification (irregular movement, inactivity, or pathway deviation, etc.), severity, location data, and contextual information such as preceding events or environmental factors. The alarm 145 may comprise audiovisual alert devices positioned throughout the indoor environment 25. In other examples, the alarm 145 may include smart home integration that utilizes existing display and audio devices, wearable notification technology synchronized with the guidance system, or dedicated alerting appliances with specialized accessibility features for users with sensory impairments.

Upon receiving the first signal 160, the alarm 145 emits at least one of an audio and video alert 165. The alerts 165 are specifically designed to address the cognitive and perceptual characteristics of individuals experiencing potential confusion or disorientation. Audio alerts employ carefully selected acoustic properties, utilizing frequency ranges (typically 500-2000 Hz) that remain accessible despite age-related hearing changes. Video alerts displayed on the video display devices 35 incorporate the use of familiar images or faces that may trigger recognition even during episodes of increased confusion. Simultaneously with the alarm activation, the processor 60 sends a second signal 170 to designated emergency contacts 175. The designated emergency contacts 175 comprise a predefined notification network of caregivers, family members, neighbors, or professional care providers who have been designated to receive alerts regarding potential safety concerns. The second signal 170 contains comprehensive information required for appropriate assessment and response by the emergency contacts 175.

Figure 11:
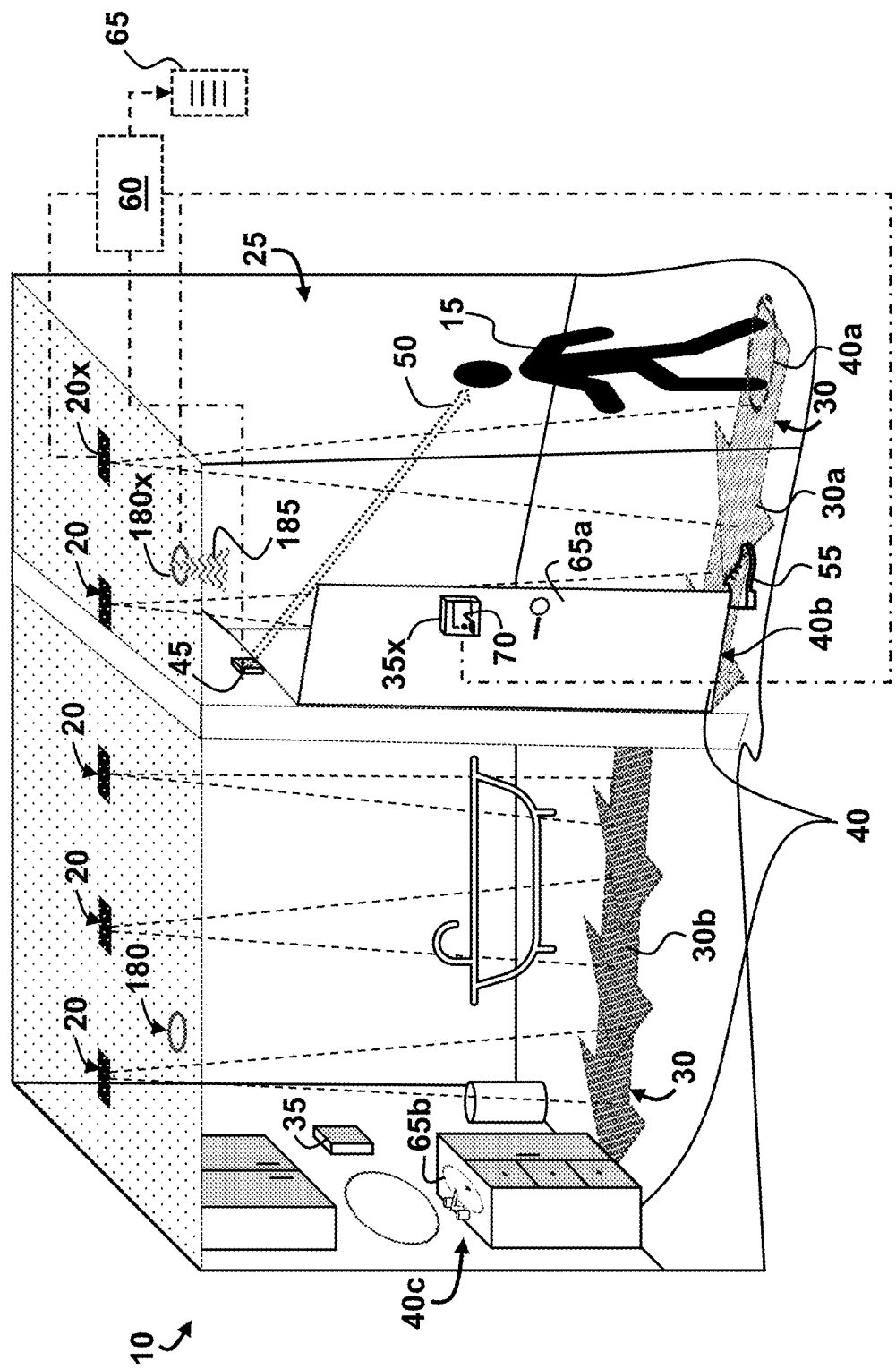
FIG. 11 is a schematic diagram illustrating a guidance system containing a speaker to provide directional audio instructions along illuminated pathways, according to an embodiment herein.

FIG. 11, with reference to FIGS. 1 through 10, illustrates that the guidance system 10 may comprise at least one speaker 180 positioned in the indoor environment 25, wherein the processor 60 is to activate selected speakers 180x to provide directional audio instructions 185 along the illuminated pathways 30; synchronize the audio instructions 185 with the task-specific instructional content 70; and adjust audio volume based on proximity to target locations 40. The directional audio instructions 185 may comprise spoken navigational instructions, musical tones that increase in frequency upon approaching the target locations 40, or verbal confirmations upon successful task completion, or a combination thereof.

The at least one speaker 180 represents a network of audio output devices positioned throughout the indoor environment 25 to create comprehensive auditory coverage with specific technical characteristics appropriate for individuals with cognitive impairments. These speakers 180 may be implemented through various forms including ceiling-mounted directional speakers, wall-mounted transducers, furniture-integrated audio elements, or parametric speakers that create focused sound beams. The speaker 180 may also be part of the user's smartphone, in an example.

The processor 60 utilizes audio routing algorithms to activate selected speakers 180x from among the distributed speaker network. The speaker selection process employs spatial mapping that correlates the user's current position 50 (as detected by environmental sensors 45 and motion sensors 115) with the known positions of available speakers 180x. This mapping enables activation of the specific speakers 180x that will provide optimal audibility from the user's current perspective, considering factors such as distance. A capability of the audio functionality of the processor 60 is the ability to synchronize the audio instructions 185 with the task-specific instructional content 70 presented on video display devices 35. This synchronization creates a unified, coherent instructional experience across distributed presentation points throughout the environment 25. For example, when a user 15 approaches an activity location 40, the processor 60 may provide a concise verbal overview of the upcoming task while the visual display prepares to show detailed step-by-step instructions. As the visual demonstration begins, the audio narration synchronizes precisely with demonstrated actions, highlighting critical elements through dual-channel reinforcement. As the user 15 approaches target locations 40, the system 10 may progressively adjust output levels using distance-mapped volume curves that balance audibility against potential startling effects from sudden volume changes. Moreover, the proximity-based volume adjustment implements distance estimation using sensor fusion techniques that combine data from multiple environmental sensors 45 and motion sensors 115.

The content of the directional audio instructions 185 may comprise spoken navigational instructions that utilize simplified linguistic structures, concrete directional terminology, and measured delivery pacing appropriate for cognitive processing limitations. These verbal instructions employ vocabulary specifically selected for familiarity and comprehension, avoiding abstract terms or complex spatial concepts that might create confusion. Alternatively or additionally, the directional audio instructions 185 may utilize musical tones that increase in frequency upon approaching the target locations 40. Another option for the directional audio instructions 185 is verbal confirmations upon successful task completion. These confirmations represent an application of positive reinforcement principles within the guidance framework, providing immediate acknowledgment that strengthens successful behavior patterns.

Figure 12:
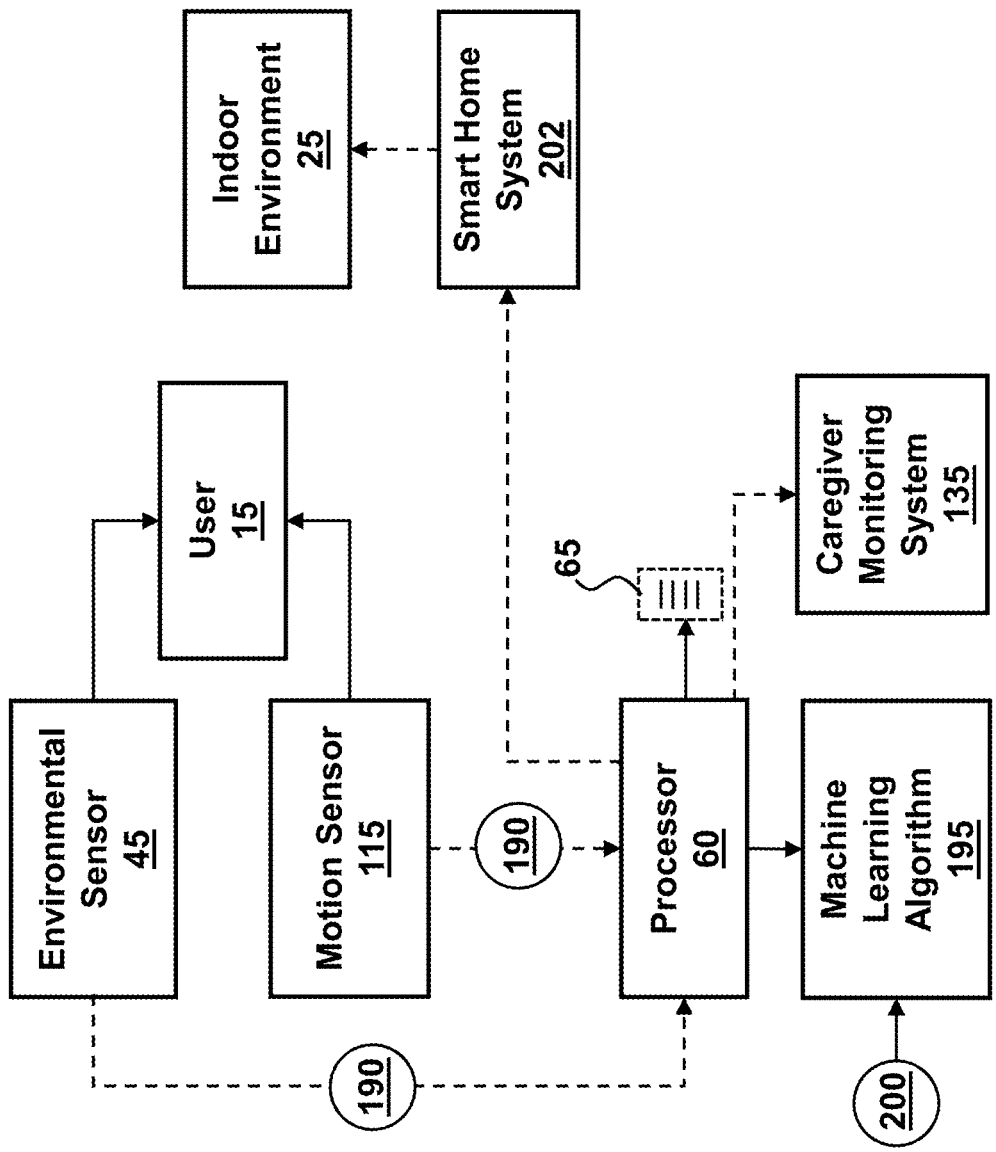
FIG. 12 is a block diagram illustrating a task guidance system with adaptive instruction levels and machine learning-based user confusion detection, according to an embodiment herein.

FIG. 12, with reference to FIGS. 1 through 11, illustrates that the processor 60 may provide specific task breakdown for completing each of the daily activities 65; adjust an instruction detail level for performing the daily activities 65 based on user performance; repeat instructions when user confusion is detected using input 190 received from at least one of the at least one environmental sensor 45 and at least one motion sensor 115 by using a machine learning algorithm 195 retrievable by the processor 60; and alert caregivers (i.e., caregiver monitoring system 135) if task completion patterns indicate declining cognitive function of the user 15 based on comparisons to learning patterns 200 of the machine learning algorithm 195. In an example, the processor 60 may integrate with a smart home system 202 to provide automated environmental control of the indoor environment 25.

At the highest level, activities 65 are segmented into major phases that represent conceptually distinct portions of the overall task. Each phase is further decomposed into specific steps that represent individual actions requiring discrete motor sequences or decisions. For activities 65 with particularly complex components, steps may be further subdivided into micro-steps that isolate elementary movements or perceptual judgments. This multi-level decomposition creates a comprehensive task representation that can be navigated at different levels of detail depending on the user's current cognitive capabilities and support needs. For example, Table I includes examples of various daily activities 65 with the corresponding steps for performing these activities 65.

TABLE I

Examples of daily routine activities and the steps for performance

| Activity | Steps |
| --- | --- |
| Washing Hands | 1. Turn on the faucet. |
| | 2. Wet hands and apply soap. |
| | 3. Rub hands together for 20 seconds. |
| | 4. Rinse. |
| | 5. Dry hands with a towel. |
| Brushing Teeth | 1. Hold the toothbrush. |
| | 2. Place a small amount of toothpaste on the brush. |
| | 3. Brush teeth gently in small circles. |
| | 4. Rinse mouth with water. |
| | 5. Wash off toothbrush and put it back in the holder. |
| Taking Medication | 1. Hold the daily pill organizer or bottle. |
| | 2. Remove correct number of pills from the organizer. |
| | 3. Fill a glass with water. |
| | 4. Place the medicine in your mouth. |
| | 5. Take a sip of water and swallow the medicine. |
| | 6. Close the container or bottle and put it back in its place. |

TABLE I-continued

Examples of daily routine activities and the steps for performance

| Activity | Steps |
| --- | --- |
| Pouring a Drink | 1. Take a cup from the cabinet and place it on the counter.<br>2. Hold the bottle/carton.<br>3. Slowly pour until the cup is half-full.<br>4. Close the bottle/carton and put it back.<br>5. Drink from the cup. |
| Making a Sandwich | 1. Take two slices of bread.<br>2. Spread peanut butter/jelly on bread.<br>3. Put the slices together.<br>4. Cut sandwich in half if needed.<br>5. Place sandwich on a plate. |
| Using the Microwave | 1. Place food in a designated microwave-safe plate/bowl.<br>2. Open the microwave and place the plate inside.<br>3. Close the door and press the timer (e.g., 1 minute).<br>4. Press start and wait.<br>5. When finished, carefully remove the plate (use oven mitts if hot). |
| Eating a Meal | 1. Sit at the table with your food.<br>2. Use utensils as needed (fork, spoon, knife).<br>3. Take small bites and chew thoroughly.<br>4. Drink between bites as needed.<br>5. When finished, place all dishes in the sink. |
| Wiping Surfaces | 1. Take a cleaning wipe or damp cloth from its packet.<br>2. Wipe counter/table surface in small circles to remove crumbs or dirt.<br>3. Discard used wipes in the trash can. |
| Washing Clothes | 1. Open the washing machine lid.<br>2. Place the dirty clothes inside the washing machine.<br>3. Pour the detergent into the detergent tray.<br>4. Close the lid.<br>5. Press the start button. |
| Watching Television | 1. Sit down on the sofa.<br>2. Pick up the remote control from the coffee table.<br>3. Press the power button to turn the television on.<br>4. Use the channel buttons to find a show you want to watch.<br>5. Adjust the volume to a comfortable level.<br>6. When finished, press the power button to turn the television off. |

The performance analysis considers multiple dimensions of task execution, including completion accuracy, execution timing, error patterns, hesitation frequency, and assistance responsiveness. These performance metrics are collected through environmental sensors 45 and motion sensors 115 during ongoing task execution, creating a comprehensive performance profile for each activity 65. The processor 60 evaluates this performance data against models of expected execution patterns, identifying specific areas where performance indicates a need for modified instructional support.

The processor 60 is configured to initiate repeated instructions when user confusion is detected or if the user 15 asks for assistance using input 190 received from at least one of the at least one environmental sensor 45 and at least one motion sensor 115. This confusion detection and responsive instruction repetition represents an application of real-time behavioral analysis specifically calibrated for the manifestations of cognitive confusion in daily activity contexts. The detection process employs a machine learning algorithm 195 retrievable by the processor 60, which implements specialized pattern recognition techniques trained on extensive datasets of confusion indicators.

The input 190 from environmental sensors 45 and motion sensors 115 provides a multi-data stream that captures both the user's physical movements and their interactions with environmental elements. Motion sensors 115 may detect behavioral indicators such as hesitation, repetitive movements, wandering patterns, or unusual activity sequences that deviate from normal task progression. Environmental sensors 45 may detect interaction anomalies such as repeated ineffective object manipulations, incorrect object selection, questions posed by the user 15, or unusual environmental disturbances associated with disorientation or searching behaviors.

The machine learning algorithm 195 employs computational techniques specifically optimized for the pattern recognition requirements of confusion detection. These techniques may include recurrent neural networks with long or short-term memory architectures that excel at identifying significant patterns in sequential data streams with variable time scales. The algorithm implements specialized feature extraction methods that transform raw sensor data into behaviorally meaningful metrics such as movement coherence scores, interaction efficiency measures, and task progression indices that serve as inputs to the classification process.

When the machine learning algorithm 195 detects patterns indicative of user confusion, the processor 60 initiates appropriate instruction repetition strategies. Rather than simply repeating previous instructions verbatim, the system 10 implements intelligent repetition that modifies presentation based on the specific confusion characteristics detected. For confusion patterns suggesting attentional issues, repetition might emphasize attention-focusing techniques such as simplified visual highlighting or targeted auditory cues. For patterns suggesting procedural memory failures, repetition might increase procedural detail while maintaining the same conceptual framing. For patterns suggesting comprehension difficulties, repetition might employ alternative explanation approaches or different vocabulary while maintaining the same instructional content.

The processor 60 is configured to alert caregivers through the caregiver monitoring system 135 if task completion patterns indicate declining cognitive function of the user 15. The detection process employs comparative analysis between current task performance patterns and established learning patterns 200 derived from the machine learning algorithm 195, enabling identification of deviations that exceed expected variation ranges. These patterns 200 incorporate multiple dimensions of cognitive functioning relevant to daily activities 65, including memory, attention regulation, sequential processing, error recognition, and adaptability to prompts. The patterns 200 are established through systematic analysis of historical performance data, identifying stable characteristics that represent the user's typical functioning across different activities, times of day, and environmental conditions.

The system 10 also provides for the integration between the processor 60 and a smart home system 202 to provide automated environmental control of the indoor environment 25. This integration extends the guidance system's capabilities beyond informational support to include physical environmental adaptation that can enhance task performance and comfort. The smart home integration creates a bidirectional information and control channel between the guidance system 10 and various environmental systems such as lighting, climate control, appliances, and security features, etc.

The environmental control capabilities enabled by this integration serve multiple functions. Task-supportive environmental adaptation automatically configures environmental conditions to optimize task performance, such as adjusting lighting levels for visual tasks, setting appropriate water temperature for hygiene activities, or pre-heating ovens for cooking tasks. Comfort management capabilities adjust environmental parameters such as temperature, humidity, and ambient lighting to maintain optimal comfort conditions based on user preferences and activity requirements. Safety enhancement features automatically monitor and adjust potentially hazardous elements such as stove burners, water temperature, or door locks based on detected user activities and capabilities.

Figure 13:
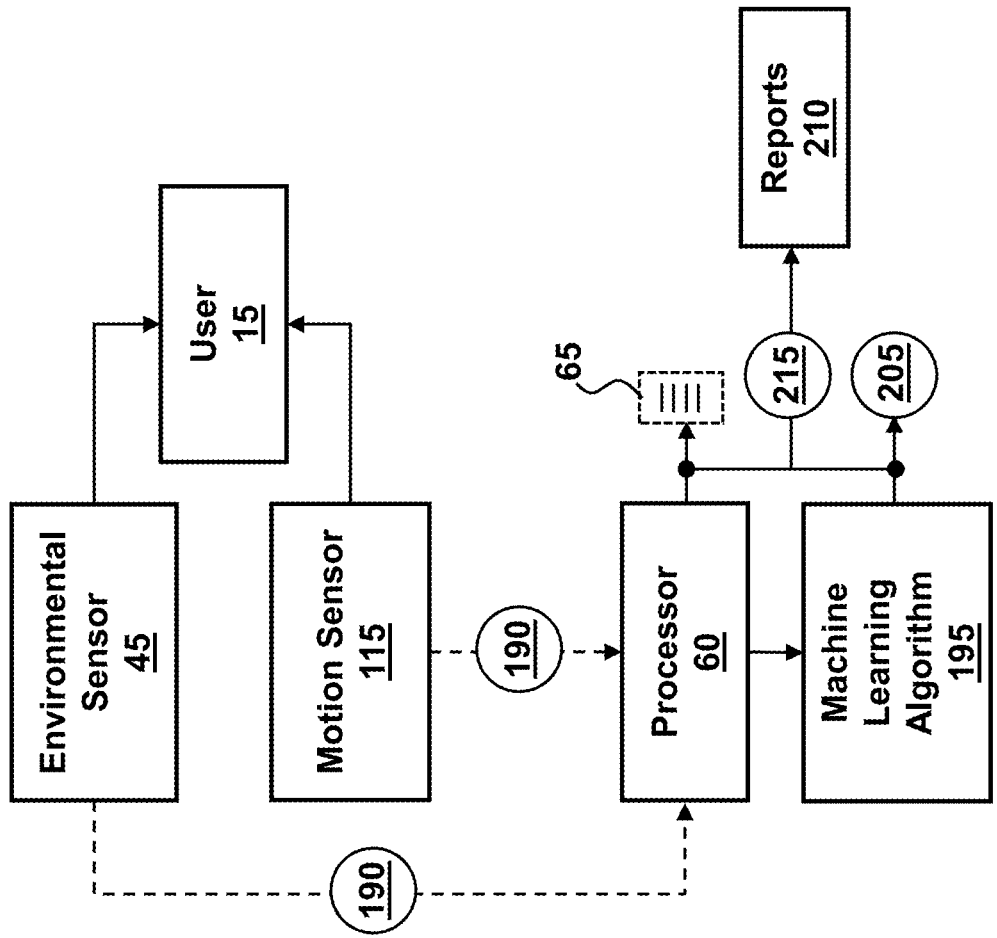
FIG. 13 is a block diagram illustrating a cognitive assessment technique using machine learning to establish normal task completion patterns and detect deviations, according to an embodiment herein.

FIG. 13, with reference to FIGS. 1 through 12, illustrates that the processor 60 may identify user-specific task completion patterns of the user 15 using input 190 received from at least one of the at least one environmental sensor 45 and at least one motion sensor 115; train a machine learning algorithm 195 retrievable by the processor 60 to establish normal task completion patterns 205 and deviations thereof in performing the daily activities 65; identify early warning signs of task confusion of the user 15 by comparing performance of completion of the daily activities 65 compared to the established normal task completion patterns 205; adapt completion criteria based on user capabilities; and generate periodic cognitive assessment reports 210 based on task performance data 215.

The identification of user-specific task completion patterns 205 requires advanced behavioral analysis techniques applied to multimodal sensor data 215. The input 190 comprises raw data streams from environmental sensors 45 and motion sensors 115, capturing diverse aspects of user behavior during task performance. Environmental sensors 45 provide detailed information about the user's interactions with objects, fixtures, and appliances, etc. throughout the indoor environment 25, including interaction timing, sequence, duration, and physical characteristics such as applied force or manipulation precision. Motion sensors 115 provide complementary data about the user's movement patterns, posture changes, and stability characteristics during mobile and stationary activities.

An aspect of the pattern identification process is its ability to differentiate between task-specific and user-specific patterns. Task-specific patterns represent behavioral elements that are primarily determined by the requirements and constraints of particular activities, while user-specific patterns represent behavioral tendencies that manifest consistently across diverse activities. Once user-specific task completion patterns have been identified, the processor 60 trains a machine learning algorithm 195 to establish normal task completion patterns 205 and deviations thereof in performing the daily activities 65. This training process transforms identified behavioral patterns into computational models that can support ongoing monitoring and assessment. The machine learning algorithm 195 may utilize various computational approaches depending on the specific pattern characteristics and assessment requirements, including supervised learning methods that utilize labeled examples of normal and atypical performance, unsupervised learning that identifies natural clusters in performance data, or reinforcement learning that progressively refines detection accuracy through continuous performance feedback.

The normal task completion patterns 205 is established through a training process that represents the user's expected performance across multiple dimensions of task execution. An aspect of the trained algorithm 195 is the processor's ability to identify early warning signs of task confusion of the user 15 by comparing performance of completion of the daily activities 65 compared to the established normal task completion patterns 205. This confusion detection functionality implements proactive monitoring that can identify subtle indicators of cognitive difficulty before they manifest as overt task failures or safety concerns.

Another capability of the processor 60 is the ability to adapt completion criteria based on user capabilities. This adaptive assessment functionality recognizes that appropriate success evaluation must consider individual capabilities rather than applying standardized benchmarks that might be inappropriate for users with cognitive impairments. The adaptation process modifies the parameters used to evaluate task completion based on the user's demonstrated capabilities, creating personalized assessment frameworks that maintain appropriate expectations while accommodating specific limitations. The processor 60 is also configured to generate periodic cognitive assessment reports 210 based on task performance data 215. These reports 210 transform the continuous monitoring data (e.g., input 190) into structured, clinically relevant information formats that support care planning and intervention decisions.

Figure 14:
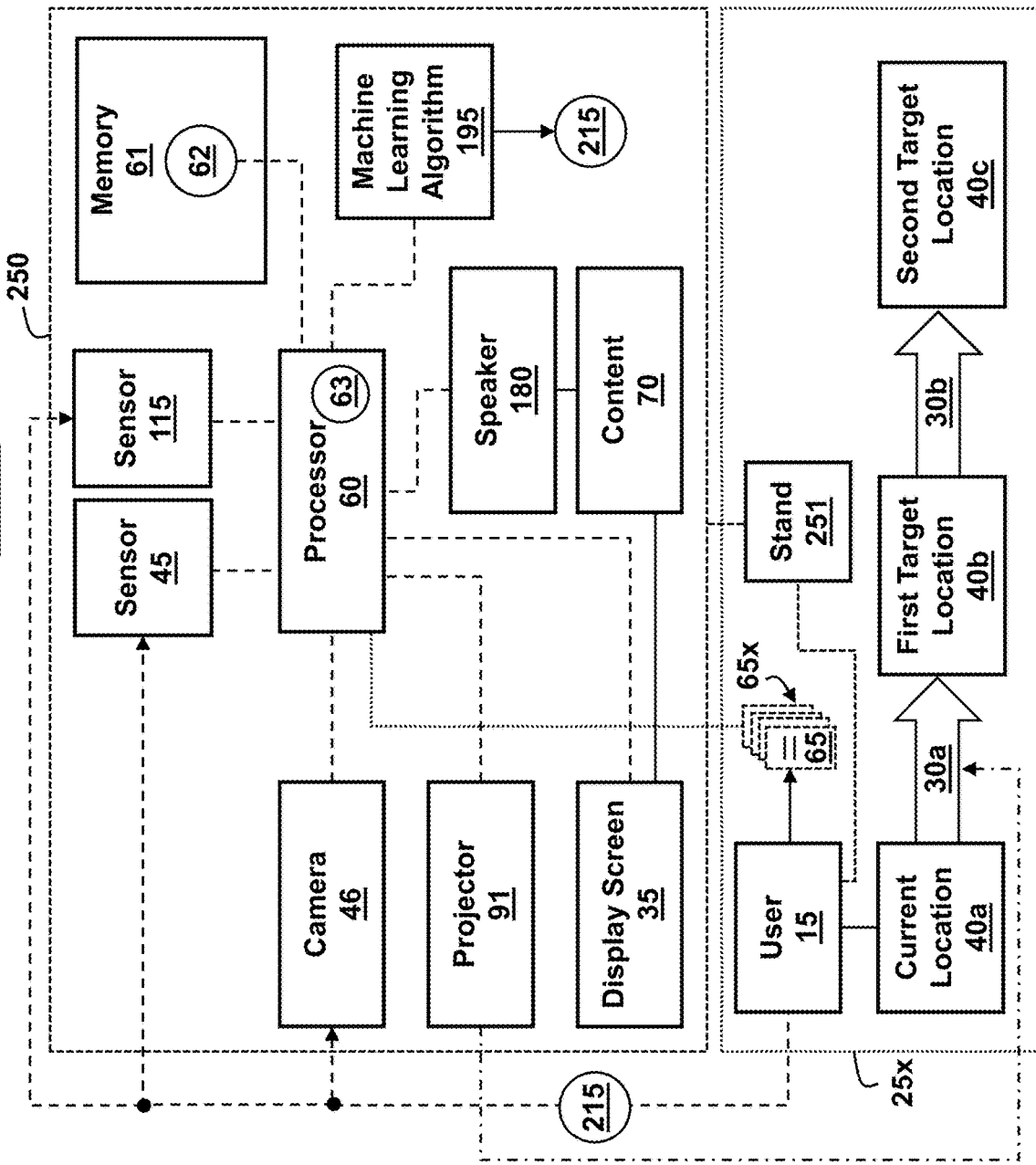
FIG. 14 is a block diagram illustrating a portable guidance device for assisting a user with cognitive impairment, according to an embodiment herein.

FIG. 14, with reference to FIGS. 1 through 13, illustrates a portable guidance device 250 for assisting a user 15 with cognitive impairment, according to an embodiment herein. The device 250 comprises a processor 60; a camera 46 operatively connected to the processor 60; at least one sensor 45, 115 operatively connected to the processor 60; a projector 91 operatively connected to the processor 60; a display screen (i.e., video display device) 35 operatively connected to the processor 60; a speaker 180 operatively connected to the processor 60; and a memory 61 storing instructions 62 that, when executed by the processor 60, cause the processor 60 to identify a current location 40*a* of the user 15 based on at least one of an image and video captured by the camera 46; instruct the projector 91 to project a first illuminated pathway 30*a* between the current location 40*a* and a first target location 40*b* based on a predefined sequence of daily activities 65 for the user 15; present at least one of task-specific audio and visual instructional content 70 through at least one of the display screen (i.e., video display device) 35 and speaker 180 for a current activity 65a in the sequence of daily activities 65; analyze activity data 215 captured by the camera 46 and the at least one sensor 45, 115 to monitor completion of the current activity 65a in the sequence of daily activities 65; deactivate projection of the first illuminated pathway 30a from the projector 91 upon detecting user arrival at the first target location 40b; verify completion of the current activity 65a using a machine learning algorithm 195 that analyzes captured activity data 215; and instruct the projector 91 to project a second illuminated pathway 30b from the first target location 40b to a second target location 40c upon verification of completion of the current activity 65a.

The camera 46 serves as the primary environmental input source and may include a microphone (not shown) to capture both audio from the environment 25x also. In the context of herein, the environment 25x may be any indoor or outdoor space. The projector 91 includes laser light sources and lenses to create the illuminated pathways 30a, 30b in the environment 25x. The memory 61 storing instructions 62 may include or access the machine learning algorithm 195.

Upon establishing the current user location 40a, the device 250 instructs the projector 91 to project a first illuminated pathway 30a between the current location 40a and a first target location 40b. Obstacle detection ensures that projected pathways route around identified impediments, creating clear guidance that avoids potential hazards. Ambient light analysis measures current lighting conditions throughout the projected path, implementing local brightness adjustments that maintain consistent visibility across lighting transitions such as shadowed areas or zones with direct sunlight. The embodiments herein support the real-time analysis of activity data 215 captured by the camera 46 and the at least one sensor 45, 115 to monitor completion of the current activity 65a. This visual activity utilizes algorithms specifically trained to recognize the actions associated with daily activities 65.

Upon detecting user arrival at the first target location 40b, the device deactivates projection of the first illuminated pathway 30a from the projector 91. This deactivation process implements fade-out effects rather than abrupt termination, providing visual continuity that avoids potentially disorienting sudden changes. The timing of deactivation is precisely coordinated with the user's arrival sequence, maintaining guidance until the user 15 is fully engaged with the target location while avoiding unnecessary projection once guidance is no longer needed. Upon verification of activity completion using the machine learning algorithm 195, the processor 60 instructs the projector 91 to project a second illuminated pathway 30b from the first target location 40b to a second target location 40c. This sequential projection implements seamless guidance transitions that maintain continuous support throughout multi-stage activity sequences.

The portable guidance device 250 provides guidance support without requiring environmental modifications or fixed installations. By consolidating sensing, processing, and guidance functionality into a single device 250 on a mobile stand 251, the device 250 enables immediate deployment across diverse environments including both familiar and novel settings. This portability extends the accessibility of cognitive guidance beyond fixed residential environments to include community spaces, healthcare facilities, or temporary accommodations, significantly expanding the contexts in which individuals with cognitive impairments can receive effective support. In an example, the portable guidance device 250 can be mounted on a height-adjustable stand 251 with wheels or other mechanisms to permit mobility. A portable battery pack (not shown) may be mounted on the stand 251 also to supply power to the device 250 for extended periods of time.

The stand 251 may utilize an auto-balancing system (not shown) with gyroscopes to maintain proper orientation of the projector 91 and sensors 45, 115 even as the device 250 is moved through the environment 25x. The device 250 can be guided by the user 15 pushing/pulling the stand 251 or can move autonomously using electric motors controlled by the processor 60 based on sensor input. The camera 46 and sensors 45, 115 may be mounted on a rotating platform (not shown) on the stand 251 that continuously scans the environment 25x to maintain spatial awareness regardless of device orientation. The projector 91 contains auto-focus capabilities to ensure properly aligned pathway projection even when the device 250 is in motion. The processor 60 continuously calibrates the alignment of the camera 46, projector 91, and sensors 45, 115 to compensate for device movement, ensuring consistent guidance functionality whether the device 250 is stationary or being relocated within the environment 25x.

In an example, the guidance device 250 may be implemented as a smartphone or tablet device running a specialized guidance application (app), where the smartphone includes the necessary components for providing guidance for the user 15. The camera 46 would be the smartphone's built-in camera, while the projector 91 would utilize the smartphone's flashlight capabilities to display the illuminated pathways 30 in the environment 25x. The environmental sensors 45 and motion sensors 115 would utilize the smartphone's existing sensor suite including its accelerometer, gyroscope, ambient light sensor, and other environmental sensing capabilities. The display screen 35 would be the smartphone's touchscreen display, while the speaker 180 would be the phone's built-in speaker system. The processor 60 and memory 61 would utilize the smartphone's processing and storage capabilities to run the application and store the machine learning algorithm 195. The guidance application would process camera and sensor data in real-time to track the user's location and activities, while projecting pathways 30 and providing audio-visual instructions through the smartphone's output systems. This smartphone/tablet implementation provides an accessible, familiar form factor that many users 15 already carry with them, eliminating the need for additional specialized hardware while maintaining the core guidance functionality through a device users are comfortable handling.

Various examples described herein may include both hardware and software elements. The examples that are implemented in software may include firmware, resident software, microcode, etc. Other examples may include a computer program product configured to include a pre-configured set of instructions, which when performed, may result in actions as stated in conjunction with the methods described above. In an example, the preconfigured set of instructions may be stored on a tangible non-transitory computer readable medium or a program storage device containing software code.

In the example of FIG. 14, the electronic device 250 includes processor 60 and computer-readable storage medium 63. Processor 60 may include a central processing unit, microprocessors, hardware engines, and/or other hardware devices suitable for retrieval and execution of instructions stored in a computer-readable storage medium 63, for example. Processor 60 may fetch, decode, and execute computer-executable instructions 62 from memory 61 to enable execution of locally-hosted or remotely-hosted applications for controlling action of the electronic device 250. The remotely-hosted applications may be accessible on other remotely-located communication devices (not shown). For example, the remote communication device may be a laptop computer, tablet device, smartphone, or notebook computer. As an alternative or in addition to retrieving and executing instructions 62, processor 60 may include electronic circuits including a number of electronic components for performing the functionality of the computer-executable instructions 62.

Alternatively, the computer-readable storage medium 63 may be any electronic, magnetic, optical, or other physical storage device that stores executable instructions 62 rather than residing in memory 61. Thus, the computer-readable storage medium 63 may be, for example, Random Access Memory, an Electrically-Erasable Programmable Read-Only Memory, volatile memory, non-volatile memory, flash memory, a storage drive (e.g., a hard drive), a solid-state drive, optical drive, any type of storage disc (e.g., a compact disc, a DVD, etc.), and the like, or a combination thereof. In one example, the computer-readable storage medium 63 may include a non-transitory computer-readable storage medium 63. The computer-readable storage medium 63 may be encoded to execute the executable instructions 62 for enabling execution of remotely-hosted applications accessed on a remote communication device. In an example, the processor 60 of the electronic device 250 executes the computer-executable instructions 62 that when executed cause the processor 60 of the electronic device 250 to perform a method 300 (described in FIGS. 15A through 15F) provided by the computer-executable instructions 62.

Figure 15C:
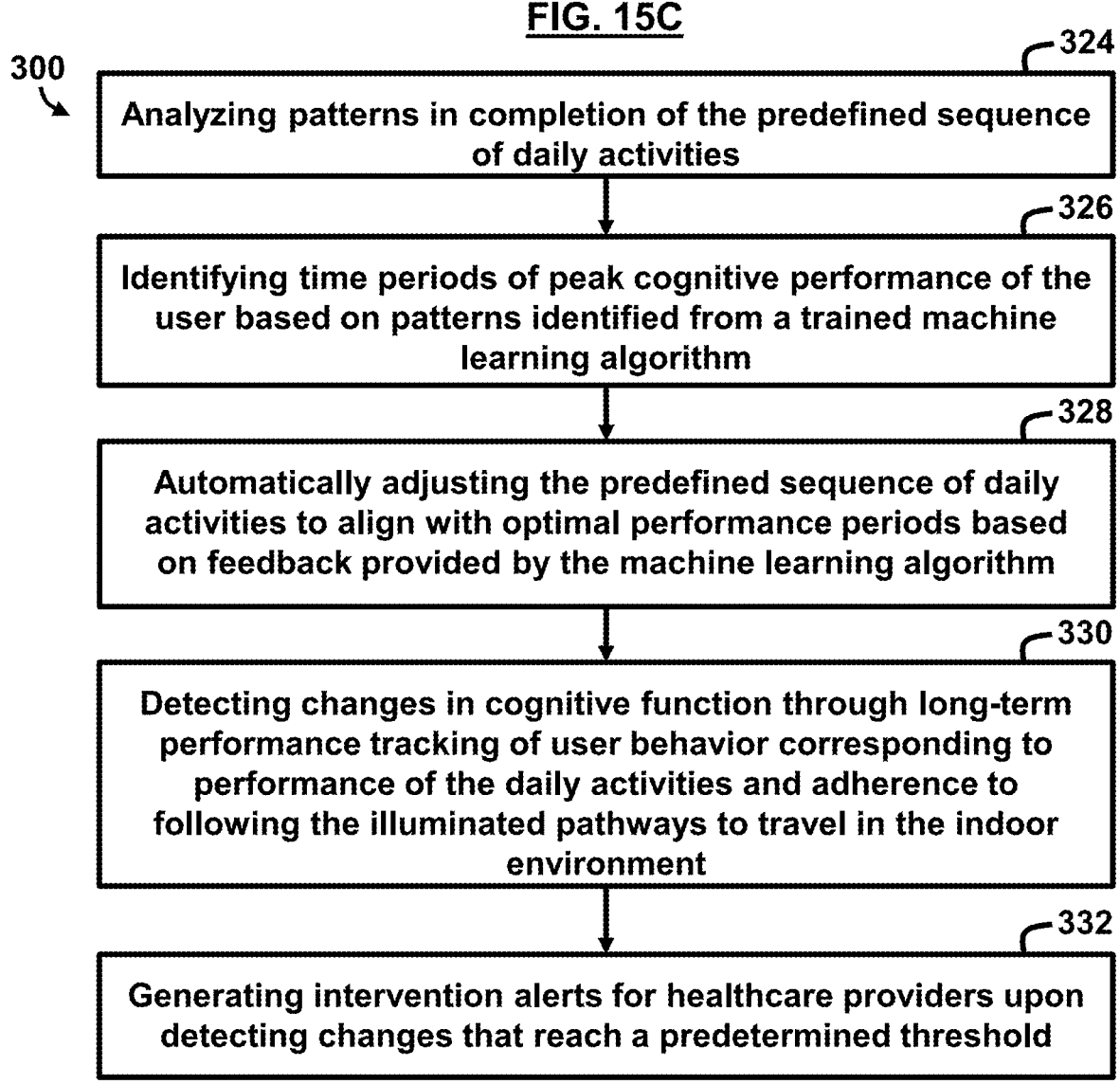
FIG. 15C is a flow diagram illustrating a method for analyzing patterns in daily activities and optimizing performance periods, according to an embodiment herein.

FIGS. 15A through 15F, with reference to FIGS. 1 through 14, are flowcharts illustrating a method 300 for utilizing illuminated pathways 30 to guide a user 15 with cognitive impairment according to another embodiment herein. As shown in FIG. 15A, the method 300 comprises storing (302) a predefined sequence of daily activities 65 for the user 15; detecting (304) a current location 40*a* of the user 15 in an environment 25*x* in real-time using at least one environmental sensor 45; activating (306) selected light-emitting elements 20*x* to create a first illuminated pathway 30*a* between the current location 40*a* and a first target location 40*b* based on the predefined sequence of daily activities 65 corresponding to the user 15; presenting (308) at least one of task-specific audio and visual instructional content 70 on a display device 35 at the first target location 40*b* for a current activity 65*a* in the sequence 65; monitoring (310) completion of the current activity 65*a* through the at least one environmental sensor 45; deactivating (312) the first illuminated pathway 30*a* upon detecting arrival at the first target location 40*b*; and advancing (314) to a next activity 65*b* in the sequence 65 upon verifying completion of the current activity 65*a* by illuminating a second pathway 30*b* to a second target location 40*c*.

The method 300 employs a multi-modal approach to activity/task completion verification, utilizing various types of environmental sensors 45 to monitor user actions and environmental changes. This verification process operates on the principle that most daily activities 65 result in detectable physical changes to the environment or observable patterns of user movement and interaction. The environmental sensors 45 may comprise a diverse array of sensing technologies, each contributing specific detection capabilities to the overall verification process. These may include motion sensors, proximity sensors, pressure sensors, object recognition cameras, thermal sensors, acoustic sensors, microphones, and specialized sensors for specific appliances or fixtures. The processor 60 integrates data from this sensor network to build a comprehensive understanding of user activity and task progression.

For activity monitoring, the method 300 utilizes a task decomposition approach, breaking each daily activity 65 into a sequence of expected steps with corresponding expected sensor inputs. For example, the task of "brushing teeth" might be decomposed into steps including: approaching the sink, turning on water, picking up toothbrush, applying toothpaste, brushing motion patterns for a minimum duration, rinsing the brush, and returning the toothbrush to its holder. Each step generates characteristic sensor data patterns that the system has been programmed to recognize.

Motion sensors 115 track the user's position 50 and movement patterns within the indoor environment 25 or other environment 25*x*. These sensors 115 detect not only the presence in specific activity locations 40 but also the micro-movements associated with task performance. For instance, when washing hands, the motion sensors 115 can detect the characteristic movements of hand rubbing, water activation, and towel use. The method 300 analyzes these movement patterns against stored templates of expected task-related movements to determine if appropriate actions are being performed. The processor 60 monitors completion of the daily activities 65 through the environmental sensors 45 and provides prompts 130 when task completion is not detected within a predetermined time period t.

The method 300 implements a machine learning algorithm 195 that is trained to recognize patterns in sensor data corresponding to successful task completion. This algorithm 195 establishes normal task completion patterns 205 for each user 15, accounting for individual variations in task performance. The algorithm 195 analyzes sensor data streams to identify signature patterns that indicate successful completion of specific activities. Over time, this machine learning approach allows the method 300 to adapt to the user's unique way of performing tasks, increasing the accuracy of completion verification.

The processor 60 identifies user-specific task completion patterns, trains the machine learning algorithm 195 to establish normal task completion patterns 205 and detect deviations, identifies early warning signs of task confusion, adapts completion criteria based on user capabilities, and generates periodic cognitive assessment reports 210 based on task performance data 215. Through this multi-modal sensing and analysis approach, the method 300 achieves reliable activity completion verification without requiring conscious user reporting or caregiver observation.

During the monitoring phase (310), the method 300 employs parallel processing to simultaneously evaluate task completion through the environmental sensors 45 while tracking the user's position 50. This concurrent assessment maintains comprehensive situational awareness throughout the activity sequence 65, enabling responsive adaptation to the user's actual progress and location. The pathway deactivation process (312) determines the optimal moment to deactivate the first illuminated pathway 30*a*. This process evaluates the user's arrival characteristics at the first target location 40*b*, ensuring that first illuminated pathway 30*a* remains present until fully engaged with the task location 40*b* but doesn't persist unnecessarily. When advancing (314) to the next activity 65*b* in the sequence 65, the method 300 implements granular progress recognition that acknowledges completion of activity components while maintaining the overall sequence context. This approach supports the illumination of the second pathway 30*b* to the second target location 40c based on verified task completion, creating a continuous guidance experience that adapts to the user's actual performance timing and patterns.

In an example, the method 300 may provide for an initial daily activation of the system 10 or device 250 to be triggered automatically based on typical wake times stored in the daily routine schedule 125. For example, at the user's typical wake time (e.g., 7:00 AM) or after a nap, etc., the processor 60 activates selected light-emitting elements 20x to create a first illuminated pathway 30a from the user's bed (i.e., current location 40a) to the first target location 40b (for example, the closet, etc.), while environmental sensors 45 monitor for signs that the user 15 is awake. This proactive guidance helps establish consistent morning routines critical for individuals with cognitive impairments.

As shown in FIG. 15B, the method 300 may comprise continuously updating (316) a three-dimensional model of the environment 25x based on data from the at least one environmental sensor 45; detecting and classifying (318) environmental conditions 55 that could obstruct the first or second illuminated pathway 30a, 30b; dynamically recalculating (320) the first or second illuminated pathway 30a, 30b based on detected obstacles; and maintaining (322) a database of frequently used items of the user 15 and their last known locations in the environment 25x.

The three-dimensional model updating process (316) enables more accurate pathway generation in partially observed environments by taking into consideration environmental conditions 55 that may impede user movement or illuminated pathway detection by the user 15. The environmental conditions classification process (318) extends beyond simple obstacle detection to include surface condition assessment, identifying potentially hazardous areas such as wet floors or uneven surfaces that might affect user safety during navigation. The dynamic recalculation process (320) evaluates potential routes based on the individual user's historical confusion patterns in specific environmental contexts, avoiding areas that have previously triggered disorientation. The maintenance (322) of the item location database utilizes data input of object positions based on established usage patterns and daily routines to establish a set of environmental conditions 55 relevant to the environment 25x, thereby enhancing the ability of the method 300 to guide users 15 to frequently needed items at appropriate times throughout their daily activities. In this context, the environmental conditions 55 may not necessarily be obstacles or hindrances to the user's ability to move about the environment 25x, but instead could any useful items necessary for the user 15 to perform the daily activities 65x.

As shown in FIG. 15C, the method 300 may comprise analyzing (324) patterns 205 in completion of the predefined sequence of daily activities 65; identifying (326) time periods of peak cognitive performance of the user 15 based on patterns 200 identified from a trained machine learning algorithm 195; automatically adjusting (328) the predefined sequence of daily activities 65 to align with optimal performance periods based on feedback provided by the machine learning algorithm 195; detecting (330) changes in cognitive function through long-term performance tracking of user behavior corresponding to performance of the daily activities 65 and adherence to following the illuminated pathways 30 to travel in the environment 25x; and generating (332) intervention alerts for healthcare providers upon detecting changes that reach a predetermined threshold.

The pattern analysis process (324) implements modeling techniques to identify cognitive performance variations across different time segments and activity types. This analysis may utilize pattern recognition algorithms that extract behavioral patterns from sensor data 190, 215. The identification (326) of peak cognitive performance periods may utilize the sensor data 190, 215 to determine when the user 15 is more active, and further uses the data 190, 215 for training the machine learning algorithm 195. Thereafter, the algorithm 195 establishes baseline cognitive functioning patterns 200.

The automatic sequence adjustment process (328) operates through an adaptive scheduling process that modifies activity timing parameters based on real-time performance metrics and historical pattern analysis. This adjustment utilizes a multi-objective optimization approach that balances cognitive capacity with therapeutic goals and practical scheduling constraints. The cognitive function change detection process (330) implements trend analysis techniques that establish personalized baseline trajectories for various cognitive domains including memory, recognition, understanding of tasks, performance, and timing. The intervention alert generation process (332) utilizes a multi-threshold triggering system with gradual escalation protocols based on both the magnitude and persistence of detected changes, where each threshold is aligned to significance levels for specific cognitive domains and is dynamically adjusted based on the user's established baseline and condition progression.

As shown in FIG. 15D, the method 300 may comprise managing transitions between the current activity 65a and the next activity 65b by providing (334) countdown timers before transition; generating (336) preparatory alerts 165 for the next activity 65b; implementing (338) graduated prompting strategies with increasing levels of assistance; confirming (340) user readiness through verbal or gestural acknowledgment; and allowing (342) task interruption and resumption with maintained progress tracking.

The countdown timer process (334) utilizes dynamic time calculation algorithms to determine appropriate pre-transition notification intervals based on the user's cognitive processing speed and attention-shifting capabilities. These timers employ variable countdown parameters that adjust based on task complexity, cognitive load of the current activity 65a, and historical transition difficulty metrics specific to the user 15. The preparatory alert generation process (336) produces transition cues that gradually intensify as the transition to the next activity and pathway approaches, beginning with subtle peripheral signals and progressing to more direct attention-capturing stimuli if initial alerts are not acknowledged. The graduated prompting strategy implementation process (338) utilizes both the information density and directiveness of prompts based on real-time assessment of user comprehension and performance. This process progresses through different levels of support, beginning with environmental cues that provide implicit guidance, advancing to explicit verbal or visual instruction if needed, and culminating in step-by-step demonstration for performing a particular activity 65a. The readiness confirmation process (340) utilizes input processing to detect and interpret verbal or gestural acknowledgments from the user 15 through natural language processing algorithms for speech pattern recognition associated with cognitive impairment conditions, and visual recognition systems trained to identify intentional gestures. The task interruption and resumption process (342) implements continuous preservation techniques that maintain comprehensive contextual data about the interrupted activity 65a, including completion status of individual steps and environmental conditions at interruption time to help facilitate a seamless approach for resuming the activity 65a.

As shown in FIG. 15E, the method 300 may comprise monitoring (344) deviations from the predefined sequence of daily activities 65; detecting (346) unsafe environmental conditions interactions using the at least one environmental sensor 45; analyzing (348) acoustic patterns for signs of user frustration or distress; identifying (350) repetitive or perseverative behaviors of the user 15; and implementing (352) context-appropriate intervention strategies to assist the user 15 in following at least one of the illuminated pathways 30 and performing the daily activities 65.

The deviation monitoring process (344) uses real-time sequence comparison algorithms that maintain a parallel tracking system of expected versus actual activity progression. This process utilizes a variance threshold that adapts to the user's established baseline adherence patterns while identifying significant deviations from these patterns that indicate cognitive deterioration versus benign variations that represent normal day-to-day fluctuations. The unsafe interaction detection process (346) integrates inputs from multiple environmental sensors 45 to identify potentially hazardous object manipulation patterns that might indicate safety risks. For example, the sensors 45 may identify situation-specific risk factors such as proximity to hot surfaces, improper handling of sharp objects, or unstable posture near fall hazards. The acoustic pattern analysis process (348) utilizes the input 215 from the sensors 45 (e.g., microphones) to identify emotional markers in vocalization patterns such as volume and intensity that are associated with frustration, confusion, or distress. This analysis may utilize natural language processing tailored for impaired speech patterns that might indicate emotional states even when verbal expression is limited. The perseverative behavior identification process (350) utilizes pattern recognition algorithms that detect cyclical or repeated movements, object interactions, or activity sequences that exceed normative repetition thresholds established for the user 15. The intervention strategy implementation process (352) selects from multiple intervention modes based on the specific type of difficulty detected, environmental conditions, and the user's historical responsiveness to different support approaches to suggest ways to assist the user 15 in performing the daily activities 65.

As shown in FIG. 15F, the method 300 may comprise monitoring (354) ambient conditions in the environment 25x affecting completion of the current activity 65a; adjusting (356) lighting levels of the first and second illuminated pathways 30a, 30b based on time of day and activity requirements; detecting (358) environmental hazards in the environment 25x using the at least one environmental sensor 45; monitoring (360) environmental conditions 55 affecting user comfort; and integrating (362) with a smart home system 202 for automated environmental control.

The ambient condition monitoring process (354) collects and processes environmental data 215 including illumination levels, acoustic properties, air quality parameters, and thermal conditions that may impact cognitive processing or task performance. This analysis correlates specific environmental parameters with established cognitive sensitivities documented for the user's particular impairment profile, identifying performance thresholds that might impede task execution or exacerbate cognitive symptoms. The dynamic pathway lighting adjustment process (356) adjusts between multiple illumination parameters including brightness, color temperature, contrast ratio, and animation characteristics that account for both natural light fluctuations and activity-specific visibility requirements. The environmental hazard detection process (358) continuously evaluates the environment 25x for potential safety concerns using inputs from the environmental sensors 45 and motion sensors 115, which may include thermal anomaly detection for identifying overheated appliances, moisture sensors for detecting slip hazards, and spatial monitoring for identifying pathway obstructions or unstable objects. The comfort condition monitoring process (360) may compare biometric indicators with environmental parameters to assess the user's physiological response to ambient conditions and suggest changes to improve the environmental comfort of the user 15. The smart home integration process (362) establishes bidirectional communication between the system 10 or device 250 with the smart home system 202 to make manage to ambient conditions such as temperature, noise control of appliances, and automated security features such as locks or security systems that adapt based on the user's current cognitive state and activity context.

Figure 16A:
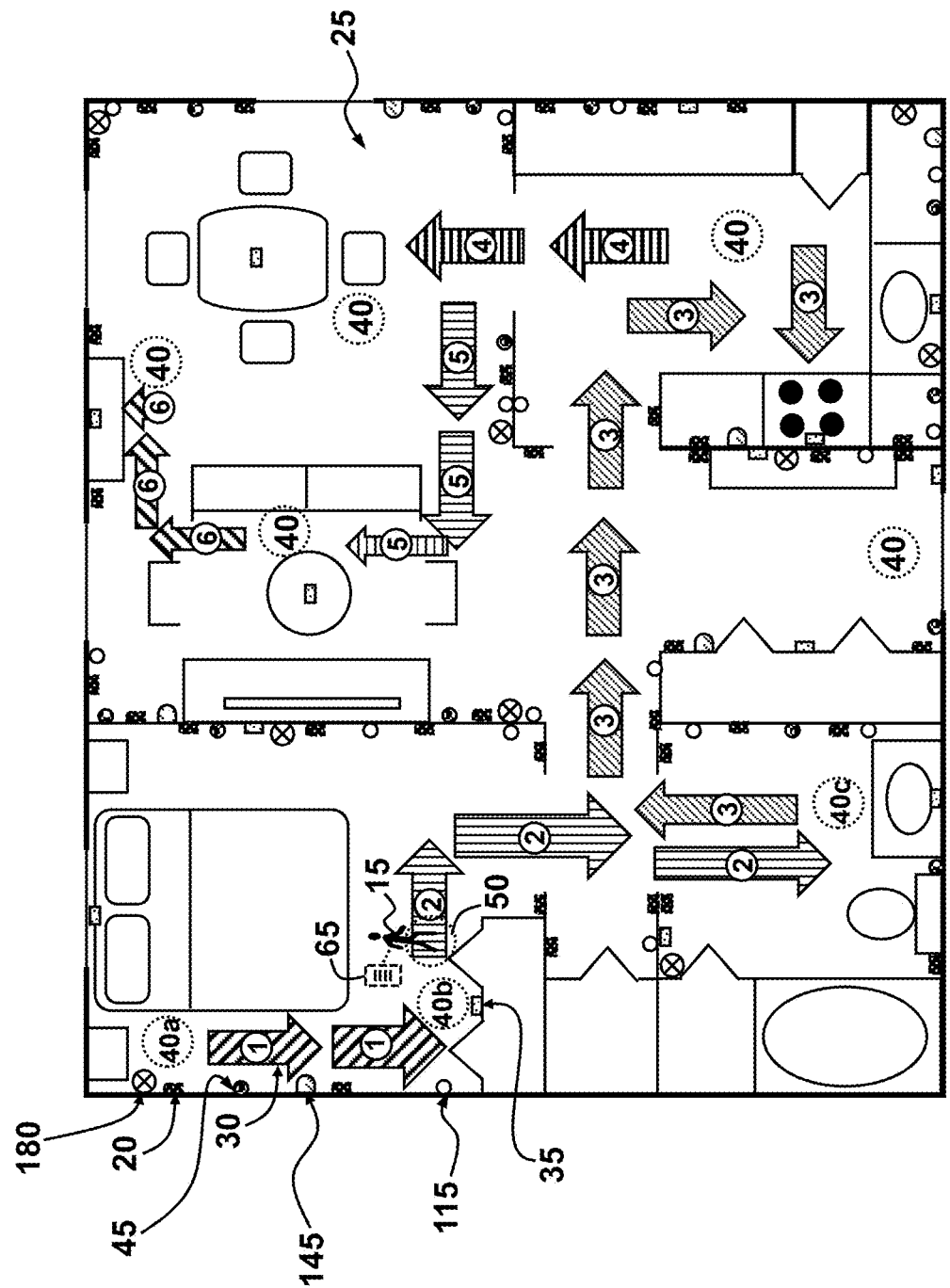
FIG. 16A is a schematic diagram illustrating a floor plan containing an integrated guidance system to guide a user with cognitive impairment, according to an embodiment herein.

FIG. 16A, with reference to FIGS. 1 through 15F, illustrates a floor plan of an indoor environment 25. In this depiction, the indoor environment 25 is fully integrated with at least one light-emitting element 20 disposed throughout an indoor environment 25, wherein the at least one light-emitting element 20 is to create illuminated pathways 30 in the indoor environment 25; at least one video display device 35 positioned at selected activity locations 40 (for example, the bathroom vanity, closet area, kitchen counters, and dining table, etc.) within the indoor environment 25; at least one environmental sensor 45 disposed in the indoor environment 25 to track user position 50 in real time and detect environmental conditions 55 in the indoor environment 25; at least one motion sensor 115 positioned throughout the indoor environment 25 to detect movement of the user 15; at least one alarm 145; and at least one speaker 180. A processor 60 (not labeled in FIG. 16A but which may be a component of any of the other devices in FIG. 16A or may be remotely located from the indoor environment 25) is to manage a predefined sequence of daily activities 65 of the user 15; activate selected at least one light-emitting element 20 to create a first illuminated pathway (labeled as pathway 1 in FIG. 16A) between a current location 40a of the user 15 and a first target location 40b of the user 15 based on predefined sequence of daily activities 65; activate the at least one video display device 35 at the first target location 40b to present at least one of task-specific audio and visual instructional content 70 (not shown in FIG. 16A) for a current activity (e.g., opening the closet in FIG. 16A, etc.) in the sequence 65; monitor completion of the current activity (e.g., opening the closet, changing clothes, and closing the closet in FIG. 16A, etc.) through the at least one environmental sensor 45; deactivate the first illuminated pathway (e.g., pathway 1 in FIG. 16A) upon detection of arrival of the user 15 at the first target location 40b; and advance to a next activity (e.g., going into the bathroom in FIG. 16A, etc.) in the sequence 65 upon verification of current activity (e.g., opening the closet, changing clothes, and closing the closet in FIG. 16A, etc.) completion by illuminating a second pathway (e.g., pathway 2 in FIG. 16A) to a second target location 40c. The process continues by guiding the user 15 through the other pathways (e.g., pathways 3, 4, 5, 6 in FIG. 16A, etc.) to provide guidance for conducting various activities at their respective locations.

The overall pathway sequence illustrated in FIG. 16A demonstrates an example of how the system 10 can guide a user 15 through a complete morning routine that might include waking up and dressing (pathway 1), personal hygiene (pathway 2), meal preparation (pathway 3), dining (pathway 4), entertainment/relaxation (pathway 5), and medication management (pathway 6), with each activity location 40 equipped with appropriate environmental sensors 45 and motion sensors 115 to verify task completion before advancing to the next stage in the sequence.

Figure 16B:
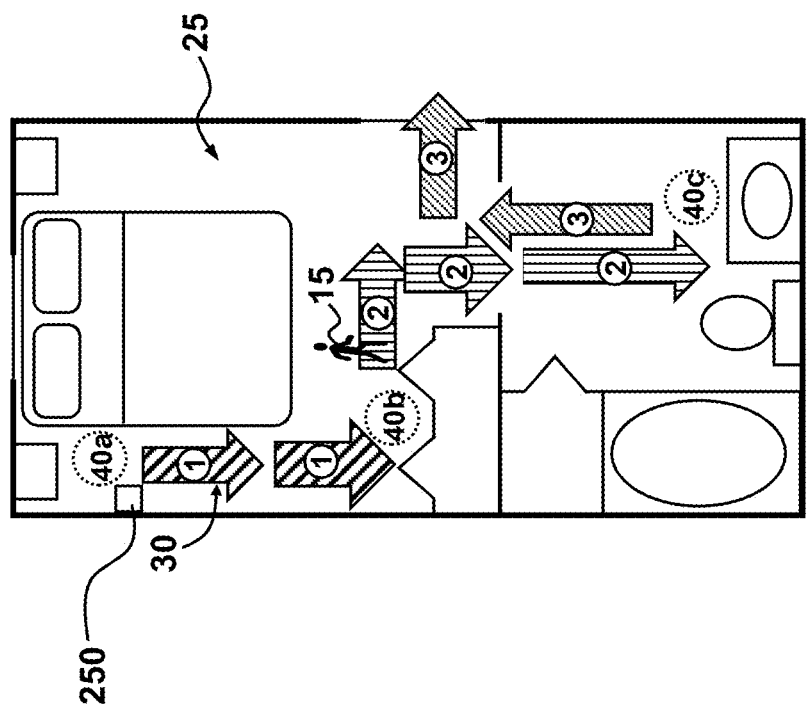
FIG. 16B is a schematic diagram illustrating a floor plan containing a portable guidance device to guide a user with cognitive impairment, according to an embodiment herein.

FIG. 16B, with reference to FIGS. 1 through 16A, illustrates a floor plan of another indoor environment 25 where the guidance device 250 is used as a portable solution for guiding a cognitively impaired individual. FIG. 16B shows an example of a smaller indoor environment 25 such as a room in a senior living facility, hospital, or other smaller area within a larger environment. The portability of device 250 allows for easy of use. However, the portable guidance device 250 could also be used in a larger setting such as the floor plan shown in FIG. 16A, which would not require the full integration of all the devices being dispersed throughout the indoor environment 25. The guiding process in FIG. 16B is similar as described above with respect to FIG. 16A in terms of the illumination of the pathways (e.g., pathways 1, 2, 3 in FIG. 16B, etc.) to guide a user 15 from a current location 40a, to a first target location 40b, and then to a second target location 40c, etc. The portable device 250 implementation demonstrates how the core functionality of pathway illumination and activity guidance can be achieved without requiring permanent installation of multiple system components throughout the environment 25. The portable device 250 projects light pathways 30 itself rather than separately installed light-emitting elements, with the projection angles calibrated to account for the specific dimensional constraints and furniture placement of the compact environment. This implementation shows how the device 250 can provide user guidance in living situations where permanent installation might not be feasible or necessary, while still delivering the structured activity guidance that helps users 15 with cognitive impairments maintain independence in daily activities. The floor plans shown in FIGS. 16A and 16B are merely examples, and other more advanced or simple floor plans can accommodate the system 10 and device 250 including both single and multi-level dwellings as well as shared spaces.

The embodiments herein may also include tangible and/or non-transitory computer-readable storage media for carrying or having computer-executable instructions or data structures stored thereon. Such non-transitory computer readable storage media can be any available media that can be accessed by a general purpose or special purpose computer, including the functional design of any special purpose processor as discussed above. By way of example, and not limitation, such non-transitory computer-readable media can include RAM, ROM, EEPROM, CD-ROM or other optical disk storage, magnetic disk storage or other magnetic storage devices, or any other medium which can be used to carry or store desired program code means in the form of computer-executable instructions, data structures, or processor chip design. When information is transferred or provided over a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable media.

Computer-executable instructions include, for example, instructions and data which cause a special purpose computer or special purpose processing device to perform a certain function or group of functions. Computer-executable instructions also include program modules that are executed by computers in stand-alone or network environments. Generally, program modules include routines, programs, components, data structures, objects, and the functions inherent in the design of special-purpose processors, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

The techniques provided by the embodiments herein may be implemented on an integrated circuit chip (not shown). The chip design is created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

The resulting integrated circuit chips can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

Furthermore, the embodiments herein can take the form of a computer program product accessible from a computer-usable or computer-readable medium providing program code for use by or in connection with a computer or any instruction execution system. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid-state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory utilized during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

Figure 17:
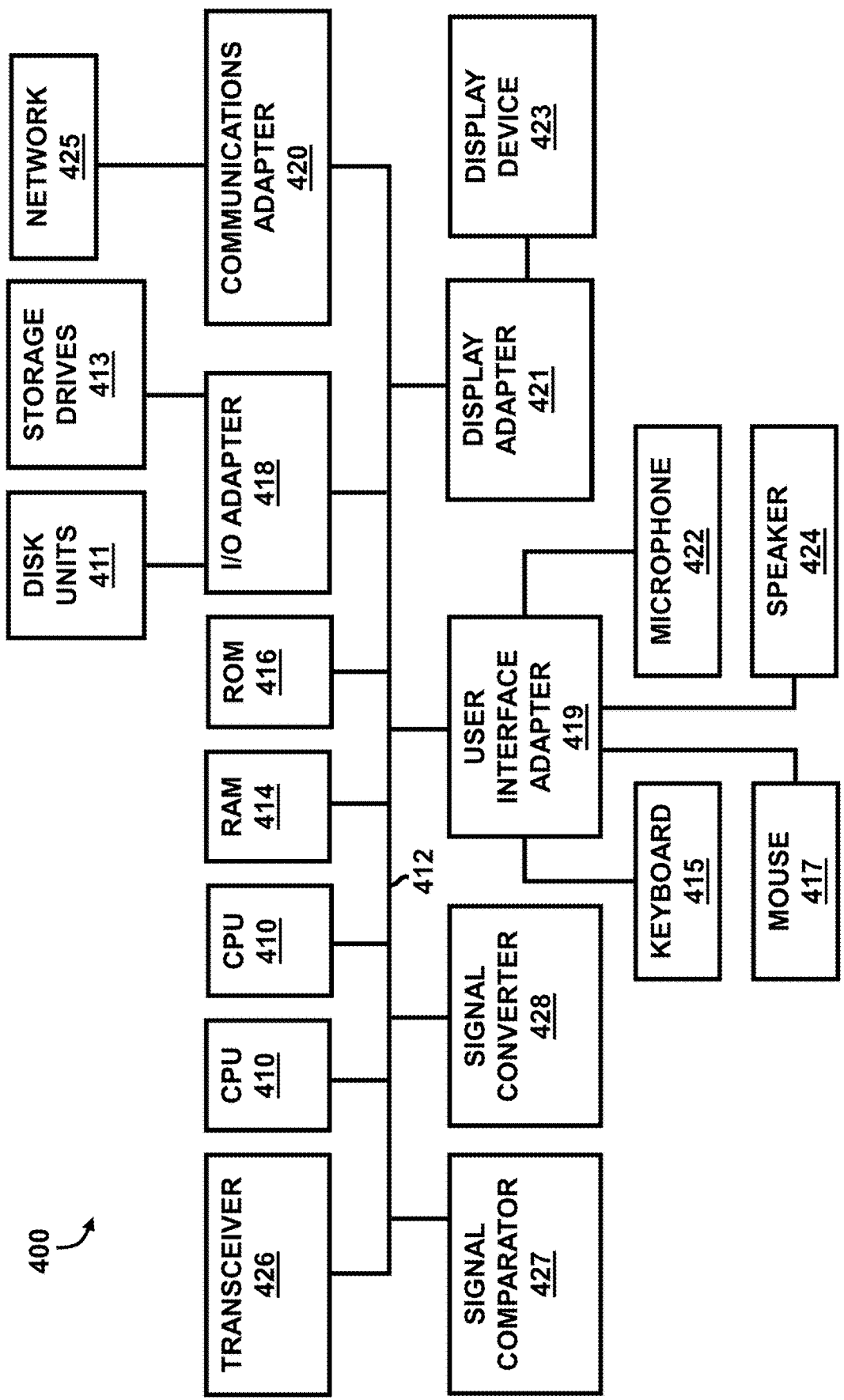
FIG. 17 is a block diagram illustrating a computer system used in accordance with the embodiments herein.

A representative hardware environment for practicing the embodiments herein is depicted in FIG. 17, with reference to FIGS. 1 through 16. This schematic drawing illustrates a hardware configuration of an information handling/computer system 400 in accordance with the embodiments herein. The system 400 comprises at least one processor or central processing unit (CPU) 410. The CPUs 410 are interconnected via system bus 412 to various devices such as a random access memory (RAM) 414, read-only memory (ROM) 416, and an input/output (I/O) adapter 418. The I/O adapter 418 can connect to peripheral devices, such as disk units 411 and tape drives 413, or other program storage devices that are readable by the system 400. The system 400 can read the inventive instructions on the program storage devices and follow these instructions to execute the methodology of the embodiments herein. The system 400 further includes a user interface adapter 419 that connects a keyboard 415, mouse 417, speaker 424, microphone 422, and/or other user interface devices such as a touch screen device (not shown) to the bus 412 to gather user input. Additionally, a communication adapter 420 connects the bus 412 to a data processing network 425, and a display adapter 421 connects the bus 412 to a display device 423 which may be embodied as an output device such as a monitor, printer, or transmitter, for example. Further, a transceiver 426, a signal comparator 427, and a signal converter 428 may be connected with the bus 412 for processing, transmission, receipt, comparison, and conversion of electric or electronic signals.

The embodiments herein provide a comprehensive solution for assisting individuals with cognitive impairments by creating an intuitive guidance system 10, portable guidance device 250, and guidance method 300 that address the challenges of spatial disorientation, task sequencing difficulties, context recognition problems, and transition management issues of such individuals. The illuminated pathways 30 serve as a visual guide to help direct the user 15 between activity locations 40 without requiring complex interpretation or understanding by the user 15. The seamless progression from one activity 65a to the next activity 65b through illuminated pathway sequences (e.g., pathways 30) provides continuous orientation support while reducing cognitive load and anxiety for the user 15. Whether implemented as a fully integrated environmental system 10 or as a portable guidance device 250, the embodiments herein enable individuals with cognitive impairments to maintain relative independence and dignity in performing daily activities 65 by providing real-time visual, audio, and instructional content 70 precisely when and where they are needed for performing various activities 65. This technological approach significantly reduces caregiver burden and costs while enhancing quality of life for users 15, potentially delaying the need for more restrictive care environments as cognitive impairments progressively worsen.

The foregoing description of the specific embodiments will so fully reveal the general nature of the embodiments herein that others may, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed utilized herein is for the purpose of description and not of limitation. Therefore, while the embodiments herein have been described in terms of preferred embodiments, those skilled in the art will recognize that the embodiments herein may be practiced with modification within the spirit and scope of the appended claims.

What is claimed is:

1. A guidance system for assisting a user with a cognitive impairment by providing an illuminated pathways, the system comprising:
   at least one light-emitting element disposed throughout an indoor environment, wherein the at least one light-emitting element is to create the illuminated pathways in the indoor environment, wherein the at least one light-emitting element comprises (i) a laser emitter to produce visible light, and (ii) a waveguide to optically direct the illuminated pathways in a plurality of angles through optical redirection;
   at least one video display device positioned at selected activity locations within the indoor environment;
   at least one environmental sensor disposed in the indoor environment to track user position in real time and detect environmental conditions in the indoor environment; and
   a processor operatively connected to the at least one light-emitting element, the at least one video display device, and the at least one environmental sensor, wherein the processor is to:
      train a machine learning algorithm by:
         collecting sensor data representing user movement patterns and environmental interactions comprising baseline behavioral data during initial system use;
         establishing baseline task completion patterns specific to baseline cognitive capabilities of the user and the baseline behavioral data;
         implementing pattern recognition algorithms to identify deviations from baseline performance; and
         establishing updated task completion patterns to align with a predefined sequence of daily activities of the user;
      manage the predefined sequence of daily activities of the user;
      activate selected light-emitting elements to create a first illuminated pathway between a current location of the user and a first target location of the user based on the predefined sequence of daily activities and the updated task completion patterns established by the machine learning algorithm;
      activate the at least one video display device at the first target location to present at least one of task-specific audio and visual instructional content for a current activity in the sequence;
      monitor completion of the current activity through the at least one environmental sensor;

deactivate the first illuminated pathway upon detection of arrival of the user at the first target location;
advance to a next activity in the sequence upon verification of current activity completion by illuminating a second pathway to a second target location; and
control (i) an operational output of the at least one light-emitting element to adjust pathway routing, intensity, and illumination characteristics, or a combination thereof, of the illuminated pathways, and (ii) the at least one of the task-specific audio and visual instructional content, based on the updated task completion patterns established by the machine learning algorithm,
wherein the machine learning algorithm establishes personalized timing thresholds based on a user performance history,
wherein the processor modifies outputs of linked hardware devices when the user does not move toward a particular illuminated pathway within an established timing threshold by increasing an illumination intensity of the at least one light-emitting element, and activating an output displayed on the at least one video display device, or a combination thereof, and
wherein the processor processes raw sensor data from the at least one environmental sensor through signal conditioning algorithms that filter noise and normalize variations in sensor response before analysis by the machine learning algorithm.

2. The guidance system of claim 1, wherein the at least one light-emitting element comprises light-emitting diodes arranged in a strip configuration along structural components within the indoor environment.

3. The guidance system of claim 1, comprising:
reflective surfaces within the indoor environment, the reflective surfaces configured to redirect the visible light beams around corners in the indoor environment.

4. The guidance system of claim 1, wherein the processor is to:
store multiple activity sequences for different times of day;
adapt sequence timing for performing the multiple activity sequences based on user performance history;
modify activity sequences based on caregiver input; and
skip or modify activities based on a health status of the user.

5. The guidance system of claim 1, comprising at least one motion sensor positioned throughout the indoor environment, wherein the processor is to:
detect movement of the user through the at least one motion sensor;
determine the current location based on the detected movement; and
generate the illuminated pathways based on the current location.

6. The guidance system of claim 1, wherein the task-specific instructional content comprises pre-recorded video demonstrations of daily living activities customized for specified target locations.

7. The guidance system of claim 1, wherein the processor is to:
access a predetermined daily routine schedule of the user;
initiate activation of the illuminated pathways at predetermined times according to the daily routine schedule; and
select appropriate task-specific instructional content to be presented on the at least one video display device based on time of day and specified target locations.

8. The guidance system of claim 1, wherein the processor is to:
monitor completion of the daily activities through the at least one environmental sensor;
provide at least one of audio and video prompts through the at least one video display device when task completion is not detected within a predetermined time period; and
send an update to a caregiver monitoring system with task completion status.

9. The guidance system of claim 7, comprising at least one alarm operatively connected to the processor, wherein the processor is to:
identify irregular movement patterns or extended periods of inactivity of the user detected by at least one motion sensor based on predetermined movement patterns or the daily routine schedule;
activate the illuminated pathways;
send a first signal to the at least one alarm to emit at least one of an audio and video alert upon detecting the irregular movement patterns, the extended periods of inactivity of the user, or that a position of the user has deviated from the illuminated pathways; and
send a second signal to designated emergency contacts.

10. The guidance system of claim 1, comprising at least one speaker positioned in the indoor environment, wherein the processor is to:
activate selected speakers to provide directional audio instructions along the illuminated pathways;
synchronize the audio instructions with the task-specific instructional content; and
adjust audio volume based on proximity to target locations.

11. The guidance system of claim 10, wherein the directional audio instructions comprise spoken navigational instructions, musical tones that increase in frequency upon approaching the target locations, or verbal confirmations upon successful task completion, or a combination thereof.

12. The guidance system of claim 1, wherein the processor is to:
provide specific task breakdown for completing each of the daily activities;
adjust an instruction detail level for performing the daily activities based on user performance;
repeat instructions when user confusion is detected using input received from at least one of the at least one environmental sensor and at least one motion sensor by using the machine learning algorithm retrievable by the processor; and
alert caregivers if task completion patterns indicate declining cognitive function of the user based on comparisons to learning patterns of the machine learning algorithm.

13. The guidance system of claim 1, wherein the processor is to:
identify user-specific task completion patterns of the user;
train the machine learning algorithm retrievable by the processor to establish normal task completion patterns and deviations thereof in performing the daily activities;
identify early warning signs of task confusion of the user by comparing performance of completion of the daily activities compared to the established normal task completion patterns;
adapt completion criteria based on user capabilities; and
generate periodic cognitive assessment reports based on task performance data.

14. A portable guidance device for assisting a user with a cognitive impairment by providing an illuminated pathways, the device comprising:
- a processor;
- a camera operatively connected to the processor;
- a sensor operatively connected to the processor;
- a projector operatively connected to the processor;
- a display screen operatively connected to the processor;
- a speaker operatively connected to the processor; and
- a memory storing instructions that, when executed by the processor, cause the processor to:
  - train a machine learning algorithm by:
    - collecting sensor data representing user movement patterns and environmental interactions comprising baseline behavioral data during initial device use;
    - establishing baseline task completion patterns specific to baseline cognitive capabilities of the user and the baseline behavioral data;
    - implementing pattern recognition algorithms to identify deviations from baseline performance; and
    - establishing updated task completion patterns to align with a predefined sequence of daily activities of the user;
  - identify a current location of the user based on the at least one of an image and video captured by the camera;
  - instruct the projector to project a first illuminated pathway between the current location and a first target location based on the predefined sequence of daily activities for the user;
  - present at least one of task-specific audio and visual instructional content through at least one of the display screen and speaker for a current activity in the sequence of daily activities and the updated task completion patterns established by the machine learning algorithm;
  - analyze activity data captured by the camera and the sensor to monitor completion of the current activity;
  - deactivate projection of the first illuminated pathway from the projector upon detecting user arrival at the first target location;
  - verify completion of the current activity using the machine learning algorithm that analyzes captured activity data;
  - instruct the projector to project a second illuminated pathway from the first target location to a second target location upon verification of completion of the current activity; and
  - control (i) an operational output of the projector to adjust pathway routing, intensity, and illumination characteristics, or a combination thereof, of the illuminated pathways, and (ii) the at least one of the task-specific audio and visual instructional content, based on the updated task completion patterns established by the machine learning algorithm,
- wherein the projector comprises (i) a laser emitter to produce visible light, and (ii) a waveguide to optically direct the illuminated pathways in a plurality of angles through optical redirection,
- wherein the machine learning algorithm establishes personalized timing thresholds based on a user performance history,
- wherein the processor modifies outputs of linked hardware devices when the user does not move toward a particular illuminated pathway within an established timing threshold by increasing an illumination intensity of the projector, and activating an output displayed on the display screen, or a combination thereof, and
- wherein the processor processes raw sensor data from the sensor through signal conditioning algorithms that filter noise and normalize variations in sensor response before analysis by the machine learning algorithm.

15. A method for utilizing illuminated pathways to guide a user with a cognitive impairment, the method comprising:
- training a machine learning algorithm by:
  - collecting sensor data representing user movement patterns and environmental interactions comprising baseline behavioral data during an initial use;
  - establishing baseline task completion patterns specific to baseline cognitive capabilities of the user and the baseline behavioral data;
  - implementing pattern recognition algorithms to identify deviations from baseline performance; and
  - establishing updated task completion patterns to align with a predefined sequence of daily activities of the user;
- storing the predefined sequence of daily activities for the user;
- detecting a current location of the user in an indoor environment in real-time using at least one environmental sensor;
- activating selected light-emitting elements to create a first illuminated pathway between the current location and a first target location based on the predefined sequence of daily activities corresponding to the user and the updated task completion patterns established by the machine learning algorithm;
- presenting at least one of task-specific audio and visual instructional content on a display device at the first target location for a current activity in the sequence;
- monitoring completion of the current activity through the at least one environmental sensor;
- deactivating the first illuminated pathway upon detecting arrival at the first target location;
- advancing to a next activity in the sequence upon verifying completion of the current activity by illuminating a second pathway to a second target location;
- controlling (i) an operational output of the selected light-emitting elements to adjust pathway routing, intensity, and illumination characteristics, or a combination thereof, of the illuminated pathways, and (ii) the at least one of the task-specific audio and visual instructional content, based on the updated task completion patterns established by the machine learning algorithm,
- establishing personalized timing thresholds based on a user performance history,
- modifying outputs of linked hardware devices when the user does not move toward a particular illuminated pathway within an established timing threshold by increasing an illumination intensity of the at least one light-emitting element, and activating an output displayed on the display device, or a combination thereof, and
- processing raw sensor data from the at least one environmental sensor through signal conditioning algorithms that filter noise and normalize variations in sensor response before analysis by the machine learning algorithm,
- wherein the light-emitting elements comprise (i) a laser emitter to produce visible light, and (ii) a waveguide to optically direct the illuminated pathways in a plurality of angles through optical redirection.

16. The method of claim 15, comprising:
continuously updating a three-dimensional model of the indoor environment based on data from the at least one environmental sensor;
detecting and classifying environmental conditions that could obstruct the first or second illuminated pathway;
dynamically recalculating the first or second illuminated pathway based on detected obstacles; and
maintaining a database of frequently used items of the user and their last known locations in the indoor environment.

17. The method of claim 15, comprising:
analyzing patterns in completion of the predefined sequence of daily activities;
identifying time periods of peak cognitive performance of the user based on patterns identified from a trained machine learning algorithm;
automatically adjusting the predefined sequence of daily activities to align with optimal performance periods based on feedback provided by the machine learning algorithm;
detecting changes in cognitive function through long-term performance tracking of user behavior corresponding to performance of the daily activities and adherence to following the illuminated pathways to travel in the indoor environment; and
generating intervention alerts for healthcare providers upon detecting changes that reach a predetermined threshold.

18. The method of claim 15, comprising managing transitions between the current activity and the next activity by:
providing countdown timers before transition;
generating preparatory alerts for the next activity;
implementing graduated prompting strategies with increasing levels of assistance;
confirming user readiness through verbal or gestural acknowledgment; and
allowing task interruption and resumption with maintained progress tracking.

19. The method of claim 15, comprising:
monitoring deviations from the predefined sequence of daily activities;
detecting unsafe environmental condition interactions using the at least one environmental sensor;
analyzing acoustic patterns for signs of user frustration or distress;
identifying repetitive or perseverative behaviors of the user; and
implementing context-appropriate intervention strategies to assist the user in following at least one of the illuminated pathways and performing the daily activities.

20. The method of claim 15, comprising:
monitoring ambient conditions in the indoor environment affecting completion of the current activity;
adjusting lighting levels of the first and second illuminated pathways based on time of day and activity requirements;
detecting environmental hazards in the indoor environment using the at least one environmental sensor;
monitoring environmental conditions affecting user comfort; and
integrating with a smart home system for automated environmental control.

* * * * *